(12) United States Patent
Raza et al.

(10) Patent No.: US 7,074,553 B2
(45) Date of Patent: Jul. 11, 2006

(54) RETROVIRUS ASSOCIATED WITH MYELODYSPLASTIC SYNDROMES AND USES THEREOF

(75) Inventors: Azra Raza, Worcester, MA (US); Harvey D. Preisler, deceased, late of Worcester, MA (US); by Azra Raza, legal representative, Worcester, MA (US)

(73) Assignee: Rush University Medical Center, Chicago, IL (US)

( * ) Notice: Subject to any disclaimer, the term of this patent is extended or adjusted under 35 U.S.C. 154(b) by 191 days.

(21) Appl. No.: 10/433,244

(22) PCT Filed: Nov. 27, 2001

(86) PCT No.: PCT/US01/44263

§ 371 (c)(1),
(2), (4) Date: May 28, 2003

(87) PCT Pub. No.: WO03/001210

PCT Pub. Date: Jan. 3, 2003

(65) Prior Publication Data

US 2004/0106103 A1    Jun. 3, 2004

Related U.S. Application Data

(60) Provisional application No. 60/253,591, filed on Nov. 28, 2000.

(51) Int. Cl.
| *C12Q 1/68* | (2006.01) |
| *C12Q 1/70* | (2006.01) |
| *C12Q 1/04* | (2006.01) |
| *C12N 7/01* | (2006.01) |
| *C12N 7/02* | (2006.01) |

(52) U.S. Cl. .............................. 435/5; 435/6; 435/7.1; 435/235.1; 435/239; 435/29; 435/34

(58) Field of Classification Search .................... 435/5, 435/6, 7.1, 29, 235.1, 239, 325, 371; 514/2, 514/44; 424/147.1, 148.1, 159.1, 160.1; 530/387.1
See application file for complete search history.

(56) References Cited

U.S. PATENT DOCUMENTS 5,140,105 A * 8/1992 Ohno ......................... 530/350
5,721,095 A * 2/1998 Chan et al. ..................... 435/5
5,817,457 A * 10/1998 Bird et al. ...................... 435/5

OTHER PUBLICATIONS

Telesnitsky et al., Methods in Enzymology, 1995, vol. 262, pp. 347-362.*
Chen et al., Leukemia, 2005, vol. 19, pp. 767-775.*

Napoli, et al., "Myelodysplasia Progressing to Acute Myeloblastic Leukemia in an HTLV-III Virus-Positive Homosexual Man with AIDS-Related Complex." *Am J Clin Path* (86), No. 6, pp. 788-791, Dec. 1986. United States. (Abstract).

Muller, et al., "Comparison of HIV-Associated Dyshemopoiesis in Myelodysplastic HIV-Negative Patients." Verhandlungen der Deutschen Gesellschaft fur *Pathologie* (74), pp. 149-154, 1990. Germany. (Abstract).

Ogawa, et al., "Increased Evi-1 Expression is Frequently Observed in Blastic Crisis of Chronic Myelocytic Leukemia." *Leukemia* (10), No. 5, pp. 788-794, 1996. Stockton Press.

Karlic, et al., "Association of Human T-Cell Leukemia Virus and Meylodysplastic Syndrome in a Central European Population." *Cancer Research* (57), No. 21, pp. 4718-4721, 1997. Baltimore, MD, Waverly Press.

Miyahara, et al., "Cytomegalovirus-Associated Myelodysplasia and Thrombocytopenia in an Immunocompetent Adult." *Ann Hematol* (74) No. 2, pp. 99-101, 1997. Springer-Verlag.

Raza. "Hypothesis: Myelodysplastic Syndromes May Have a Viral Etiology." *Int J Hematology* (68), No. 3, pp. 245-256, 1998. Elsevier Science Ireland Ltd.

Raza, "Myelodysplastic Syndromes May Have an Infectious Etiology." *J Tox Env Health Part A* (61), No. 5-6, pp. 387-390, 2000. Taylor & Francis.

Raza, "Consilience Across Evolving Dysplasias Affecting Myeloid, Cervical, Esophageal, Gastric and Liver Cells: Common Themes and Emerging Patterns." *Leukemia Research* (24), No. 1, pp. 63-72, 2000. Elsevier Science, Ltd.

Mundle, et al., "Presence of Activation-Related m-RNA for EBV and CMV in the Bone Marrow of Patients with Myelodysplastic Syndromes." *Cancer Letters* (164), No. 2, pp. 197-205, 2001. Elsevier Science, Ltd.

* cited by examiner

*Primary Examiner*—David Guzo
(74) *Attorney, Agent, or Firm*—Foley & Lardner LLP

(57) ABSTRACT

The present invention relates first, to the identification of a novel retrovirus and the novel nucleotide sequences encoding a retroviral polymerase gene (POL nucleotides) associated with the existence of MDS and MDS associated disorders. The present invention further relates to methods for using the MDS associated retroviral nucleotides for the detection of MDS and MDS associated disorders in patient samples. The present invention also relates to methods for using and targeting the MDS associated retroviral POL nucleotides in gene therapy protocols for the treatment of MDS and MDS associated disorders in patients in need of such treatment. The present invention further relates to diagnostic protocols and kits for the detection of MDS and MDS associated disorders in tissue samples.

16 Claims, 8 Drawing Sheets

Early progenitor CD34+ cell showing VLP
In the cytoplasm

Cylindrical Confronting Cisternea (CCC) & VLP seen next to each other

Size of the particle in 108 nm

VLP in MDS

Cultured BM Bx plate on patient positive for RT assay

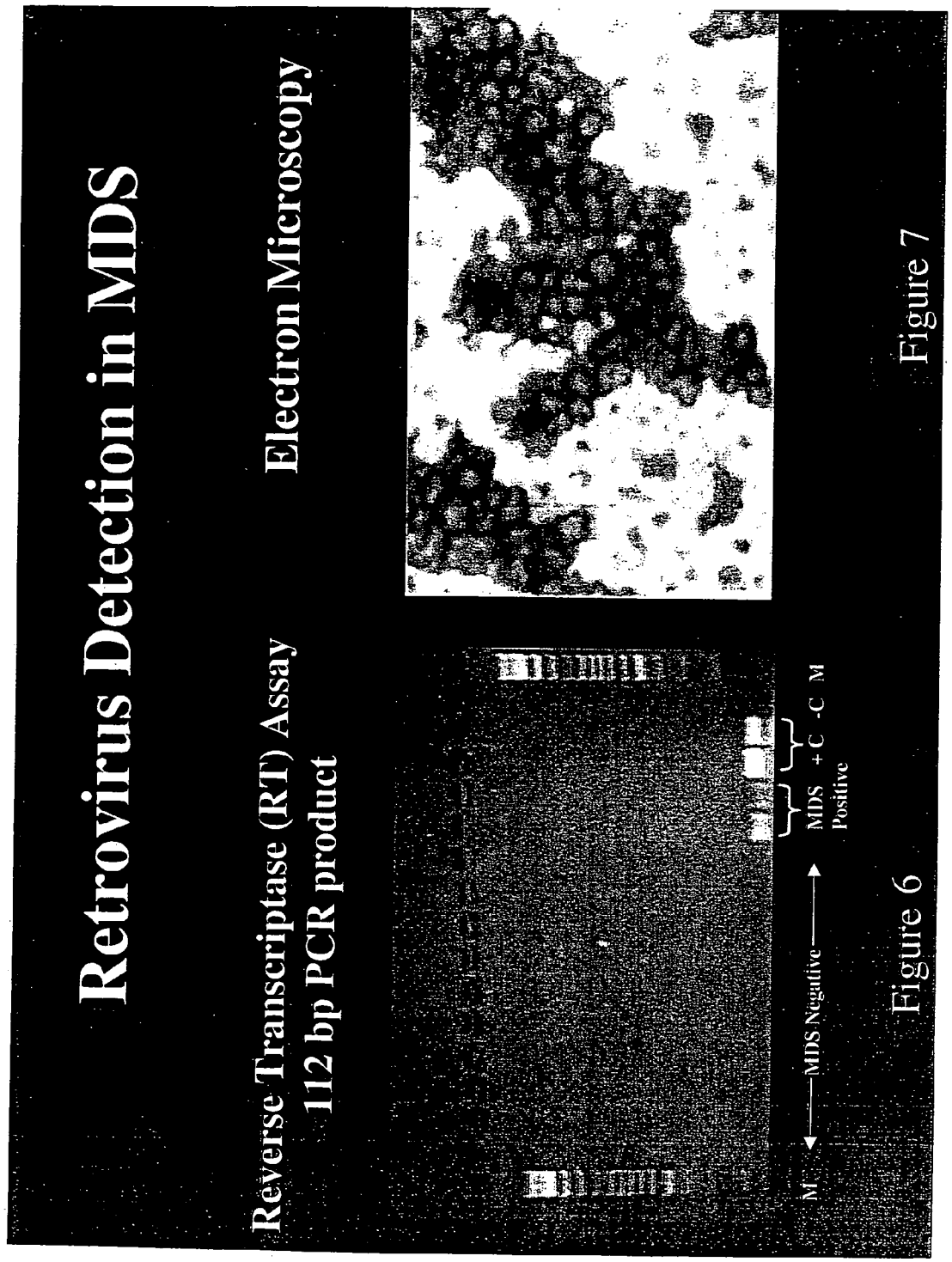

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial
<220> FEATURE:
<223> OTHER INFORMATION: Primer

<400> SEQUENCE: 1
accattcctt tagctgccca                                              20

<210> SEQ ID NO 2
<211> LENGTH: 21
<212> TYPE: DNA
<213> ORGANISM: Artificial
<220> FEATURE:
<223> OTHER INFORMATION: Primer

<400> SEQUENCE: 2
gcctttacta taccagccat a                                            21

<210> SEQ ID NO 3
<211> LENGTH: 20
<212> TYPE: DNA
<213> ORGANISM: Artificial
<220> FEATURE:
<223> OTHER INFORMATION: Primer

<400> SEQUENCE: 3
ccttagctga gcaagactgt                                              20

<210> SEQ ID NO 4
<211> LENGTH: 20
<212> TYPE: DNA
<213> ORGANISM: Artificial
<220> FEATURE:
<223> OTHER INFORMATION: Primer

<400> SEQUENCE: 4
ctttcactgt tccagccctt                                              20

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
tcaactctgt cctcttctgc                                              20

<210> SEQ ID NO 6
<211> LENGTH: 20
<212> TYPE: DNA
<213> ORGANISM: Artificial
<220> FEATURE:
<223> OTHER INFORMATION: Primer
```

```
<400> SEQUENCE: 6
ccttctctgt gccttctgtt                                              20

<210> SEQ ID NO 7
<211> LENGTH: 26
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (21)..(21)
<223> OTHER INFORMATION: n is a, c, g, or t

<400> SEQUENCE: 7
wshcchtgga ayacwcchrt nttygt                                       26

<210> SEQ ID NO 8
<211> LENGTH: 27
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 8
cartggaarg ntttnccnca rggnatg                                      27

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
wkrsywcswr gkaawkgy                                                18

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
ahdkkktkkv wcagykarrg                                              20

<210> SEQ ID NO 11
<211> LENGTH: 20
<212> TYPE: DNA
<213> ORGANISM: Artificial
<220> FEATURE:
<223> OTHER INFORMATION: Primer
```

```
-continued

<400> SEQUENCE: 11
ryrrgaagrs aywcwrhwgr                                          20

<210> SEQ ID NO 12
<211> LENGTH: 21
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (19)..(19)
<223> OTHER INFORMATION: n is a, c, g, or t

<400> SEQUENCE: 12
mnwrwrswrr rywttsyank g                                        21

<210> SEQ ID NO 13
<211> LENGTH: 21
<212> TYPE: DNA
<213> ORGANISM: Artificial
<220> FEATURE:
<223> OTHER INFORMATION: Primer

<400> SEQUENCE: 13
rwrmawrtcr tccatrtaht g                                        21

<210> SEQ ID NO 14
<211> LENGTH: 19
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (14)..(14)
<223> OTHER INFORMATION: n is a, c, g, or t

<400> SEQUENCE: 14
rsaadgtdyt dccncargg                                           19

<210> SEQ ID NO 15
<211> LENGTH: 20
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t

<400> SEQUENCE: 15
cctygnggha rhachttsya                                          20

<210> SEQ ID NO 16
<211> LENGTH: 21
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
```

-continued

```
<220> FEATURE:
<221> NAME/KEY: misc_feature
<222> LOCATION: (12)..(12)
<223> OTHER INFORMATION: n is a, c, g, or t

<400> SEQUENCE: 16
gtnttysymr tnaaraarrm r                                              21
```

RETROVIRUS ASSOCIATED WITH MYELODYSPLASTIC SYNDROMES AND USES THEREOF

This application is a national stage application of International Application PCT/US01/44263, filed Nov. 27, 2001, which claims priority to U.S. Provisional Patent Application Ser. No. 60/253,591, filed Nov. 28, 2000, the entire contents of both of which are hereby incorporated by reference.

INTRODUCTION

The present invention relates first, to the identification of a novel retrovirus and associated reverse transcriptase activity associated with the existence of myelodysplastic syndromes (MDS). The present invention further relates to methods for using the novel retrovirus and its associated reverse transcriptase activity and retroviral nucleotides for the detection of MDS in patient samples. The present invention further relates to nucleotide sequences encoding the MDS associated retrovirus, in particular novel nucleotide sequences encoding a retroviral polymerase gene associated with MDS and acute leukemia. The present invention also relates to methods for using and targeting the novel retrovirus and associated reverse transcriptase activity, alone or in combination with other therapeutics, for the treatment of MDS in patients in need of such treatment. The present invention further relates to diagnostic protocols and kits for the detection of MDS in tissue samples.

BACKGROUND OF THE INVENTION

The myelodysplastic syndromes (MDS) represent a group of perplexing, heterogeneous, hematological disorders characterized by the clinical paradox of variable cytopenias despite generally cellular bone marrows in the setting of monoclonal hemopoiesis. (Resegotti L. 1993. *Haematologica* 25(3):191–204; Yoshida Y. et al. 1993. *Int J Hematol* 57:87–97.) There are two types of MDS, one for which no cause is known called primary MDS, and the other which follows known and documented exposure to toxic/chemical agents such as chemotherapy or radiation, called secondary MDS. The vast majority of patients constituting approximately 90% in all, belong to the primary MDS category, while in 10% cases, the disease is a result of damage to the marrow produced by chemicals such as chemotherapy for a prior malignancy or exposure to radiation. The incidence of MDS clearly increases with age as well as following exposure to known marrow toxins. (Aul C., et al. 1992. *Br J Haematol* 82:358–67.) Frequently encountered with the incidence of MDS are progressively mutated clones reflecting a stepwise accumulation of genetic damage (Jacobs A. 1987. *Br J Cancer Review* 55:1–5), as well as confounding immunological defects represented by the detection of circulating immune complexes, lowered T-cell counts and accompanying immune disorders. (Colombat P. H., et al. 1988. *Cancer* 61:1075–81.) MDS sporadically has been found to co-exist with or follows a diagnosis of multiple myeloma (Mufti G. J., et al. 1983. *Br J Haematol* 54:91–6) or Fanconi's anemia (Auerback A. D. and Allen R. G. 1991. *Cancer Genet Cytogenet* 15:1–12).

MDS patients present with a lowering of one or more type of these blood cells (WBCs, RBCs, or platelets), the most common cell type affected being red cells, so that anemia is the universal hallmark of this disease. It is referred to as a "refractory" anemia because the anemia of MDS patients is "refractory" to or does not respond to the commonly used therapies for anemia such as iron, and/or vitamins. Lowering of the blood cells is known as "cytopenia," and therefore MDS patients may suffer from monocytopenia (lowering of only one cell-type), or bi-cytopenia (two cell-types), or tri-cytopenia (three cell-types). Patients with MDS present with one or more of the following abnormalities in the blood: anemia or RBC count; leukopenia or low WBC count, and thrombocytopenia or low platelet count.

All patients with MDS show "dysplastic" or abnormal looking cells in their marrows, however they are in all stages of maturation. In a normal marrow, the immature cells or "blasts" constitute less than 5% of the total population, and in approximately two-thirds of MDS patients as well, the blasts continue to be at this low level. In addition, red cell precursors in the blood can show iron deposits in the form of a ring around the nucleus of the cell, and such cells are called "ringed sideroblasts." A third of MDS cases however, present with more than 5% blasts in the marrow, and they are said to have "excess blasts." This excess in blasts can range from 6% to 29%, and the patient is still classified as having MDS, but if this count reaches 30%, then the disease is no longer MDS, but is said to have "transformed into acute leukemia."

Oftentimes MDS eventually transform into acute myeloid leukemia (AML). Incidence of transformation to AML appears to be highly correlated with the percentage of blasts in the bone marrow (BM) at presentation (Sanz G. F., et al. 1989. *Blood* 74:395–408), as well as certain complex cytogenetic abnormalities (Morel P., et al. 1993. *Leukemia* 7:1315–21). However, not infrequently, refractory anemia (RA) patients have been noted to progress directly to AML without an orderly, expected progression through RA to RA with excess blasts (RAEB) to AML. (Layton D. M. and Mufti G. J. 1986. *Blut* 53:423–36.)

While the disease presents with low blood counts, the real abnormality lies in the organ which is responsible for producing these abnormal or "dysplastic" cells, that is the bone marrow. The bone marrow contains a large quantity of stem cells, so called because they give birth to the blood cells. MDS is a disease in which something has gone wrong with one of the stem cells, making it dysplastic, so that all its daughters are similarly affected and look dysplastic. The affected stem cell can divide faster than its normal counterparts, and therefore rapidly fills up the compartment in the bone marrow which is responsible for producing cells that eventually come out in the blood. With time, all the cells in the blood, and almost 99% of cells in the marrow of MDS patients are descended from the transformed, abnormal parent.

Conventionally, MDS have been considered to be slowly proliferative disorders. Perhaps the most unexpected initial observation in this context emerged following studies related to the proliferative activity of hematopoietic cells in MDS bone marrows. In vivo measurement of the cell-birth rate in the bone marrow aspirate and biopsies of these patients following infusions of thymidine analogues iodo- and/or bromodeoxyuridine (IudR/BrdU) showed that contrary to expectation, the bone marrows are not only filled with large numbers of S-phase cells (median labeling index=30%), but that the doubling time of myeloblast was found to be almost twice as rapid (33 versus 56 h) as that for AML. (Raza A., et al. 1997. *Exp Hematol* 25:530–5.) It was this observation of intensive proliferative activity in the marrows of MDS patients that led to the hypothesis that persistent cytopenias in this setting could be the results of either excessive intramedullary premature apoptosis of hemotopoietic cells or abnormally prolonged retention of parenchyma cells in the marrow. Yoshida had hypothesized that ineffective hematopoiesis in MDS could be due to excessive apoptosis (Yoshida Y. 1993. *Leukemia* 7(1):144–6). Clark and Lampert actually provided morphological evidence of increased apoptotic bodies in MDS patients (Clark D. M. and Lampert I. A. 1990. *Leuk Lymphoma* 2:415–8). Several techniques to quantify the incidence of apoptosis accurately in MDS marrows were employed, including: in situ end labeling (ISEL), terminal deoxynucleotidyl transferase-mediated UTP nick end labeling (TUNEL), flow cytometric assays and the detection of low- and high-molecular weight 'DNA ladders' by gel and pulsed field electrophoresis, respectively. (Raza A., et al. 1995. *Am J Hematol* 48:143–54; Raza A., et al. 1995. *Blood* 86(1):268–76; Raza A., et al. 1996. *Int J Oncol* 8:1257–64; Alvi S., et al. 1996. *Proc Am Assoc Cancer Res* (Abstr # 185) 37:27.) Results obtained uniformly supported the hypothesis. Not only were parenchyma cells belonging to all three lineages apoptotic in MDS patients, but large numbers of cells actively engaged in DNA synthesis were also found to be simultaneously undergoing programmed cell death reflecting 'signal antonymy.' (Mundle S., et al. 1994. *J Histochem Cytochem* 42(12):1533–7.) Therefore, in summary, while the marrows of MDS patients are choking with proliferating cells, these cells are frequently in the process of concomitantly committing suicide, thus accounting for the paradox of cytopenia despite hypercellular marrows.

It appears that the excessive death of cells in the bone marrow is being mediated by certain proteins called "cytokines" which are normally produced during inflammatory responses, but which are present in higher than normal concentrations in MDS marrows. The most important of these cytokines is called Tumor Necrosis Factor or TNF. In other words, high TNF levels in the marrows induces a suicidal program in cells so that instead of being released into the blood, these cells die in the marrows. Thus, even though the bone marrow is working overtime to produce more and more blood cells, they are "ineffective" since they begin to die prematurely.

Due to the complexity of MDS, no single therapeutic approach appears to have made a significant impact on survival of patients with MDS. (Cazzola M., et al. 1998. *Haematologica* 83:910–935; Santini V. and Ferrini P. R. 1998. *Br J Haematol* 102:1124–1138.) Allogeneic bone marrow (BM) transplantation, a choice available to few patients given that the median age at diagnosis is approximately 70 years, has been the only curative therapy available. (Ratanatharathom V. et al. 1993. *Blood* 81:2194–2199; Anderson J. E., et al. 1996. *Blood* 87:51–58.) Other options have ranged from supportive care to the use of stem cell transplantation. Based on the assumption that the cytopenias may reflect a primary bone marrow failure, colony-stimulating growth factors with overlapping activities designed to stimulate proliferation of hematopoietic progenitors have been extensively investigated. (Vadhan-Raj S., et al. 1987. *N Engl J Med* 317:1545–1552; Negrin R. S., et al. 1990. *Blood* 76: 36–43; Greenberg P., et al. 1993. *Blood* 82(suppl 1): 196a.) The problem is that administered as single agents, granulocyte-macrophage colony-stimulating factor (GM-CSF) or G-CSF rarely improves the anemia and the thrombocytopenia so commonly the pathognomonic features of MDS. Erythropoietin alone produces an improvement in the anemia of approximately 20% of patients, which increases to almost 50% when combined with G-CSF. (Hellstrom-Lindberg E. 1995. *Br J Haematol* 89:67–71; Hellstrom-Lindberg E., et al. 1998. *Blood* 92:68–75.) However, only a proportion of patients respond, the response is usually temporary, and there is some concern related to an incidence of accelerated transformation. (Hermann F., et al. 1989. *Leukemia* 3:335–338.)

Acute leukemia-like intensive induction therapies have been attempted in patients with high-risk MDS (those with excess blasts or chronic myelomonocytic leukemia), with as many as half the patients achieving complete remission. (Cheson B. D. 1998. *Leuk Res* 22:17–21; Hiddemann W., et al. 1998. *Leuk Res* 22:23–26.) Short duration of remission marked by a relentless return of MDS cells in most patients, treatment-related complications or mortality, frequent encounters with drug-resistant clones, and the morbidity caused by the appearance of unexpected and unusual opportunistic infections reflecting the enormously compromised state of the immune system in these patients make the intensive chemotherapy option less desirable. In summary, save for allogeneic transplantation, MDS is a universally fatal illness, and no single approach has either altered the natural history of the disease or improved survival.

Given the biologic complexity and the unpredictable course of the disease ranging from chronic, insidious, and slowly progressive cytopenia to a rapidly evolving, lethal transformation to acute leukemia, it is not surprising that therapeutic options range widely between supportive care to intensive induction-type chemotherapy. Clearly, a better understanding of the basis for cytopenias in MDS is critical to design therapies tailored for individual needs.

SUMMARY OF THE INVENTION

The present invention relates, first, to the discovery, identification, and characterization of a novel retrovirus and its associated reverse transcriptase activity that is associated with MDS. The novel reverse transcriptase activity and associated virus of the present invention are retroviral in origin and are indicative of a MDS associated retrovirus which bears a strong correlation with MDS and acute leukemia. Samples of MDS bone marrow biopsy stromal cells containing this virus have been deposited with the American Type Collection under the Budapest Treaty, 10801 University Blvd., Manassas, Va. 20110–2209 on Nov. 28, 2000, under ATCC Accession Nos. PTA-2733 and PTA-2734. Upon the granting of a patent, all restrictions on the availability to the public of the deposited cultures will be irrevocably removed.

The present invention is based, in part, on the Applicants' discovery of a retrovirus associated with MDS and acute leukemia. Applicants observed similarities between Acquired Immune Deficiency Syndrome (AIDS) and MDS, including excessive cytopathic effect causing profound cytopenias and dysplastic morphology of the hematopoietic cells, in particular in bone marrow. Biopsies from patients with MDS and acute leukemia were grown in culture, and stromal fibroblasts were expanded by subcultures for molecular and electron microscopic (EM) studies. The EM studies demonstrate that 2–4% cultured fibroblasts contain nuclear inclusion bodies, which are indicative of virally infected tissue. The EM studies of stroma cells teased from bone marrow biopsies demonstrates that up to 40% of fibroblasts contain multiple nuclear inclusion bodies.

The Applicants' results have further demonstrated that reverse transcriptase activity has been detected in the supernatants of cultured stroma obtained from patients with MDS and acute leukemia and the presence of retroviral particles has been confirmed by EM analysis of the supernatant. Further, cell free supernatants were filtered through a 0.22 µM Millipore filter and centrifuged over a linear sucrose gradient, fractions were collected and assayed for reverse transcriptase activity. That the novel virus is a retrovirus is further indicated by its density in the sucrose gradient which is 1.14 to 1.16.

Electron microscopy of ultrathin sections of virus producing cells obtained from at least four different MDS patients demonstrate viral particles which are approximately 40 to 60 nm in diameter. The viral particles can be characterized as intracytoplasmic A type particles, which particles bear close resemblance to mouse mammary tumor virus (MMTV) particles. The EM studies demonstrate virus particles with two ring structures and spikes, in addition to immature viral particles budding at the cell surface. The morphology and size of the MDS associated viral particles is clearly distinct from HIV, which is a lentivirus, and HTLV, which has type A particles.

The present invention encompasses cells infected with the MDS associated retrovirus and cells and cell lines which support MDS associated retroviral infection and replication. The present invention further encompasses isolated preparations or cell-free preparations of the MDS associated retrovirus.

The present invention also encompasses serum from patients infected with the MDS associated retrovirus, in addition to antibodies, both polyclonal and monoclonal, raised against the MDS associated retrovirus, which may be used as diagnostic tools for the detection of MDS and related disorders.

The present invention encompasses nucleic acid molecules which comprise the following nucleotide sequences: (a) nucleotide sequences comprising the MDS associated retroviral sequences; and (b) nucleotide sequences that encompass portions or fragments of the MDS associated retroviral nucleotides which can be utilized as probes or primers in the methods of the invention for identifying and diagnosing individuals at a risk for, or exhibiting MDS and acute leukemias.

The invention also encompasses the expression products of the nucleic acids molecules listed above; i.e., proteins and/or polypeptides that are encoded by the above MDS associated retroviral nucleic acid molecules, or by degenerative, e.g., allelic variants thereof.

The compositions of the present invention further encompass antagonists of the MDS associated retroviral gene products, including small molecules, large molecules, and antibodies that exhibit anti-retroviral activity as well as nucleotide sequences that can be used to inhibit MDS associated retroviral gene expression, e.g., antisense, ribozyme molecules, and gene or regulatory sequence replacement constructs.

The present invention relates to therapeutic methods and compositions for treatment and prevention of diseases and disorders associated with the presence of the MDS associated retrovirus and reverse transcriptase activity, including but not limited to, MDS and associated leukemias. The therapeutic methods and compositions of the present invention are designed, in part, to combine (a) currently used protocols for the treatment of MDS, such as GM-CSF, G-CSF and EPO; or (b) thalidomide, with therapeutic methods and compositions which target and inhibit retroviral replication and infection. In particular, the therapeutic methods and compositions of the present invention are designed to target the MDS associated retroviral reverse transcriptase activity, such as small and large molecules and nucleoside analogs with anti-retroviral activity and retroviral nucleotides nucleotides, such as antisense molecules and ribozymes. The therapeutic methods and compositions of the present invention are also designed to target MDS associated retroviral gene products, including small molecules, large molecules, and antibodies. The present invention further relates to the vaccine formulations based on isolated MDS associated virus particles in an attenuated form and/or MDS associated retroviral gene products for the treatment and/or prevention of disorders associated with the presence of MDS associated retroviral nucleotides, such as MDS and acute leukemias.

In addition, the present invention is directed to methods that utilize the serum and antibodies raised against the MDS associated retrovirus and the nucleotide sequences of the present invention for the diagnostic evaluation, genetic testing and prognosis of MDS associated retroviral infection and/or associated disorders including, but not limited to MDS and acute leukemias. For example, in one embodiment, the invention relates to methods of diagnosing MDS associated retroviral infection and/or associated disorders MDS and acute leukemias, wherein such methods comprise measuring MDS associated retroviral gene expression in a patient sample suspected of exhibiting such a disorder. In one embodiment, nucleic acid molecules of the present invention can be used as primers for diagnostic PCR analysis for the identification of MDS associated retroviral nucleotides which correlate with the presence of a MDS associated retrovirus and/or associated disorders including MDS and acute leukemias. In yet another embodiment, nucleic acid molecules of the present invention can be used as primers for therapeutic PCR analysis in order to monitor the presence of a MDS associated retrovirus in a patient's sample in order to determine the effectiveness of a therapeutic protocol.

Moreover, the invention encompasses methods for screening compounds that can be used to treat or prevent MDS or leukemias, more specifically for compounds that inhibit viral replication or otherwise neutralize the MDS associated virus.

DEFINITIONS

As used herein, a "cell infected with MDS associated virus" refers to cells having a characteristic dysplastic morphology. EM studies show that these cells contain nuclear inclusion bodies. Reverse transcriptase activity is detected in the supernatant from cells infected with MDS associated virus and EM shows that retroviral particles are present in the supernatant.

As used herein, the term "MDS" refers to a group of acquired hematopoietic disorders with evidence of trilineage dysplasia and an approximately 30% incidence of eventual transformation into acute myeloid leukemia (AML). MDS are a group of acquired clonal hematopoietic disorders characterized by peripheral cytopenias and a normocellular or hypercellular bone marrow. The clonal hematopoietic disorders generally affect individuals exposed to marrow toxins and those in whom there is evidence of an immunocompromised state. They are more common in the elderly. The clinical presentation is marked by a variable cytopenia, although anemia is the most commonly encountered abnormality. As used herein, the term "MDS related disorders" refers to myelodysplastic and myeloproliferative disorders manifested or associated with or related to MDS and the leukemias arising from these myelodysplastic and myeloproliferative disorders. These disorders include but are not limited to: thrombocytopenia, refractory anemia (RA), RA with excess blasts (RAEB) or RAEB in transformation (RAEB-t), B-cell lymphoma of the brain, BOOP-like pulmonary disease, angiogenesis, Behcet's disease, IgA nephropathy, rheumatoid arthritis, inflammatory bowel disease, various associated skin lesions, Hodgkin's disease and other hematologic malignancies, Griscelli syndrome, mycotic abdominal aortic aneurysm, gastric cancer and colon polyps, and abnormal megakaryopoiesis.

As used herein, the term "MDS associated retroviral activity" refers to characteristic activity of retroviruses such as reverse transcriptase activity that can be detected in cells infected with the MDS associated retrovirus. MDS associated retroviral activity can be identified by EM studies, reverse transcriptase assays or immunological assays.

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, a-anomeric forms thereof, peptide nucleic acids (PNAs), and the like, that are capable of specifically binding to a target polynucleotide. The specific binding is determined by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides that range in size from a few monomeric units, e.g., 3–4, to several tens of monomeric units. Whenever an oligonucleotide is represented by a sequence of letters, such as "ATGCCTG," it will be understood that the nucleotides are in 5'>3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. It is clear to those skilled in the art when oligonucleotides having natural or non-natural nucleotides may be employed, e.g., where processing by enzymes is called for, usually oligonucleotides consisting of natural nucleotides are required. "Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding. It also includes known types of modifications, for example, labels which are known in the art, methylation, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, *Chemical Reviews* 90: 543–584 (1990), or the like, with the only proviso that they are capable of hybridization. Such analogs include synthetic nucleosides designed to enhance binding properties, reduce degeneracy, increase or decrease specificity, and the like.

As used herein, a polynucleotide "derived from" a designated sequence refers to a subset of the designated sequence of approximately at least about 6 nucleotides, preferably at least about 8 nucleotides, more preferably at least about 10–12 nucleotides, and even more preferably at least about 15–20 nucleotides. "Corresponding" means homologous to or complementary to the designated sequence. Preferably, the sequence of the region from which the polynucleotide is derived is homologous to or complementary to a sequence which is unique to an MDS associated viral genome. More preferably, the derived sequence is homologous or complementary to a sequence that is unique to all or to a majority of MDS associated viral isolates. Whether or not a sequence is unique to the MDS associated viral genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including retroviruses. The correspondence or non-correspondence of the derived sequence to other sequences can also be determined by hybridization under the appropriate stringency conditions. Hybridization techniques for determining the complementarity of nucleic acid sequences are known in the art, and are discussed infra. See also, for example, Maniatis et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

The term "recombinant polynucleotide" as used herein intends a polynucleotide of genomic, cDNA, semisynthetic, or synthetic origin. The term further intends that the polynucleotide (1) is not associated with all or a portion of a polynucleotide with which it is associated in nature; (2) is linked to a polynucleotide other than that to which it is linked in nature; or (3) does not occur in nature.

As used herein, the "sense strand" of a nucleic acid contains the sequence that has sequence homology to that of mRNA. The "anti-sense strand" contains a sequence which is complementary to that of the "sense strand."

The term "primer" as used herein refers to an oligomer which is capable of acting as a point of initiation of synthesis of a polynucleotide strand when placed under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer is extended by the polymerizing agent to form a copy of the analyte strand. The primer may be single-stranded, or alternatively may be partially or fully double-stranded.

The terms "analyte polynucleotide" and "analyte strand" refer to a single- or double-stranded nucleic acid molecule which is suspected of containing a target sequence, and which may be present in a biological sample. As used herein, the term "oligomer" refers to primers and to probes. The term oligomer does not connote the size of the molecule.

As used herein, the term "probe" refers to a structure comprised of a polynucleotide which forms a hybrid structure with a target sequence, due to complementarity of at least one sequence in the probe with a sequence in the target region. The polynucleotide regions of probes may be composed of DNA, and/or RNA, and/or synthetic nucleotide analogs. Included within probes are "capture probes" and "label probes." Preferably the probe does not contain a sequence complementary to sequence(s) used to prime the polymerase chain reaction (PCR).

As used herein, the term "target region" refers to a region of the nucleic acid which is to be amplified and/or detected. The term "target sequence" refers to a sequence with which a probe or primer will form a stable hybrid under desired conditions.

As used herein, the term "viral RNA," which includes MDS associated RNA, refers to RNA from the viral genome, fragments thereof, transcripts thereof, and mutant sequences derived therefrom.

As used herein, a "biological sample" refers to a sample of tissue or fluid isolated from an individual. Thus, "biological sample," includes but is not limited to, for example, bone marrow, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

DETAILED DESCRIPTION OF THE DRAWINGS

FIGS. 1A and 1B shows a MDS BM (bone marrow) biopsy at different magnifications. Shown is a very early progenitor cell resembling a CD34+cell. The cell harbors the viral particles (arrow) in the cytoplasm. Another particle is also observed just outside the cell. In particular, FIG. 1A shows the viral like particle (hereinafter "VLP") present in the cytoplasm of the cell.

FIG. 2 shows a micrograph of a MDS BM biopsy. In this micrograph both the VLP pointed out by the short arrow and footprints of the virus are seen next to each other. Observance of the presence of cylindrical confronting cisternae (hereinafter "CCC") that is considered as an ultrastructural marker for retroviral infection was noted and indicated by the long arrow. The size of the VLP is approximately 103 nm.

FIGS. 3A and 3B show VLPs in the BM biopsy of an MDS patient. In FIG. 3A, an immature budding viral particle can be seen. FIG. 3B depicts a cell in the vicinity where the viral particle was seen.

FIG. 6 shows the detection of MDS associated retrovirus by the reverse transcriptase assay. A 112 bp PCR product indicates the presence of retrovirus in patients with MDS on a 2% agarose gel.

FIG. 7 shows the detection of MDS associated retrovirus by electron microscopy.

DETAILED DESCRIPTION OF THE INVENTION

Figure 1A:
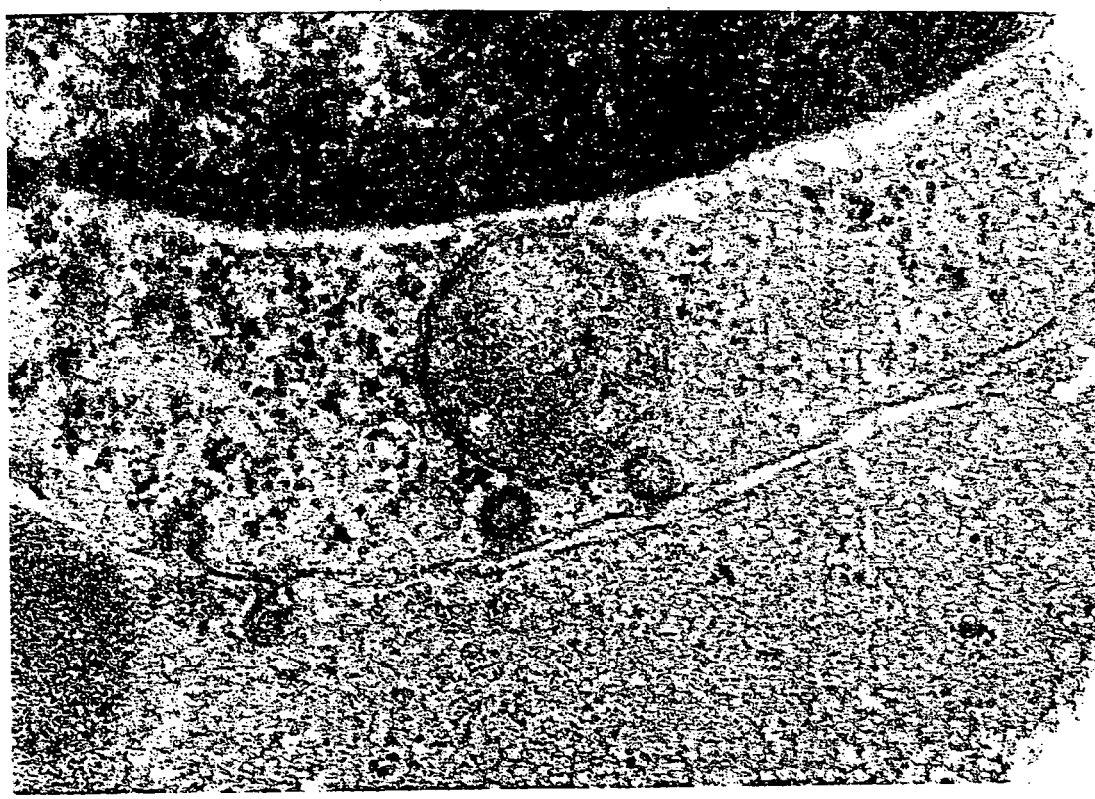
Figure 1B:
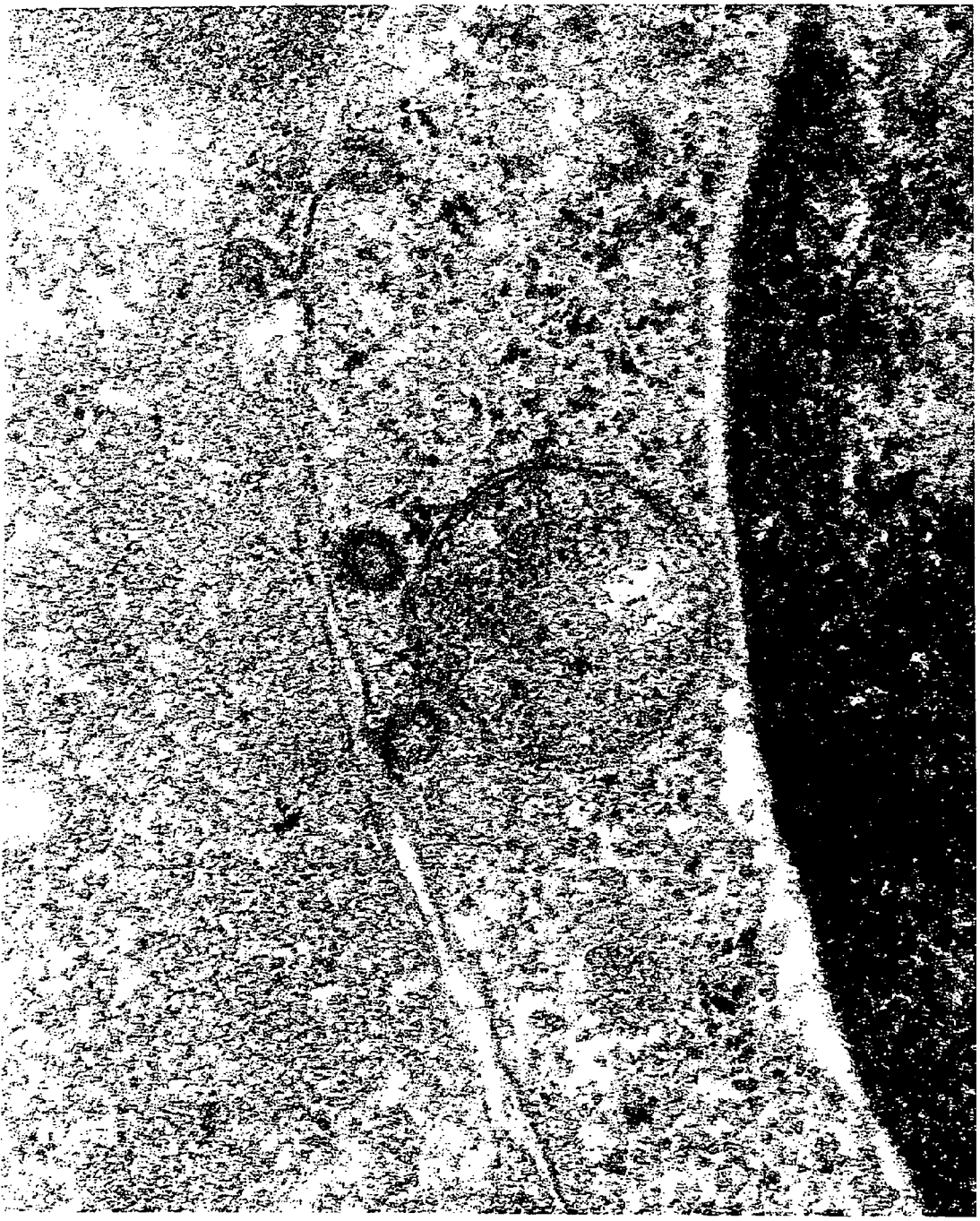
Figure 2:
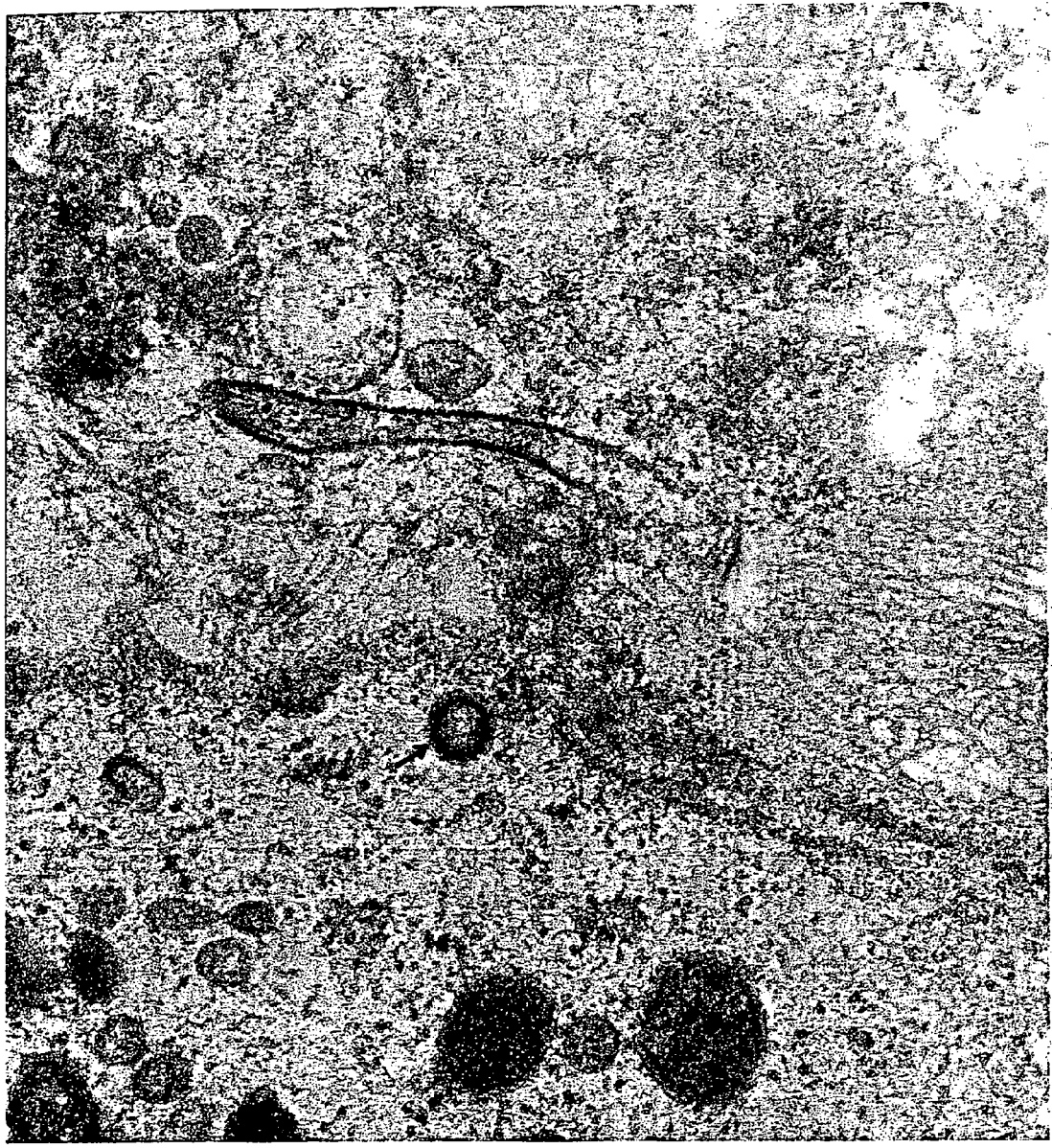
Figure 3A:
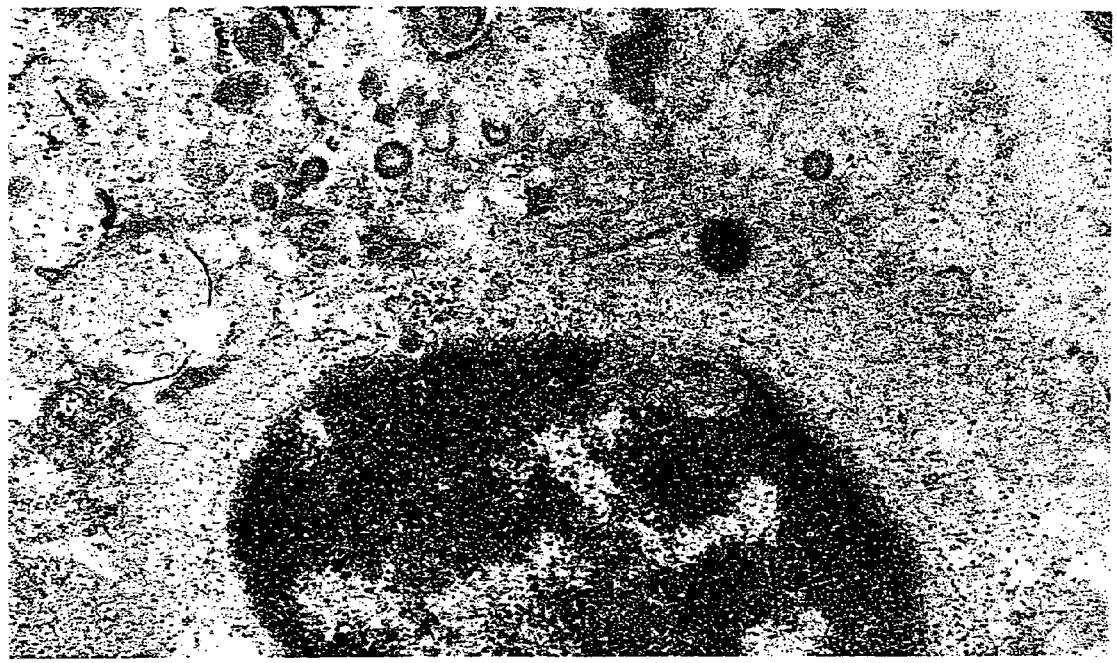
Figure 3B:
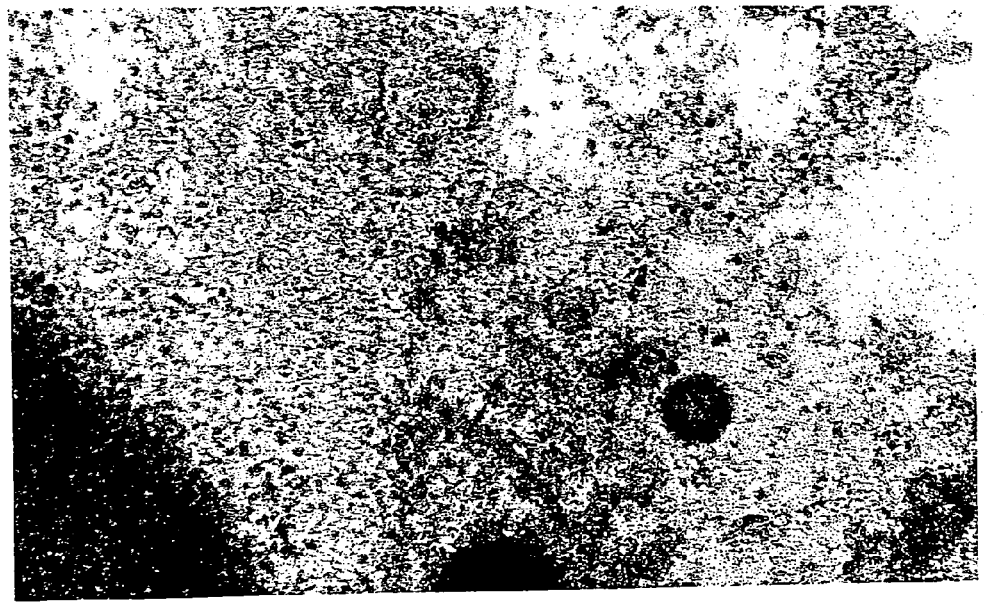

The present invention is based on the discovery, identification and characterization of a MDS associated retrovirus isolated from bone marrow tissue samples of patients with MDS and acute leukemia. A pure preparation of virus was obtained from bone marrow samples of patients with MDS and acute leukemia. The virus was purified by filtering a supernatant of virally infected cells, obtained from a patient with MDS and acute leukemia, through a 0.22 µM Millipore filter. The filtered supernatant was centrifuged on a sucrose gradient, samples of which were assayed for reverse transcriptase activity. Samples having a density of between 1.14 and 1.16 were shown to have reverse transcriptase activity. EMs of the isolated virus demonstrate that the viral particles are intracytoplasmic A type particles, which structurally resemble mouse mammary tumor virus (MMTV) particles.

The present invention relates to extracts of the MDS associated retrovirus that can be recognized immunologically from patients afflicted with MDS and whose bone marrow biopsy cultures indicate a reverse transcriptase activity. Any type of immunological assay may be employed, in particular immunofluorescence, immunoenzymatic or radioimmunoprecipitation are examples of the types of assays which may be employed in connection with the present invention.

The present invention relates to isolated cell free preparations of the MDS associated retrovirus. The present invention also relates to the total RNA isolated from these preparations. The RNA isolated from MDS associated retrovirus has been converted to cDNA using random primers corresponding to pol regions of known retroviruses, MMTV, HTLV-1 and HIV, and reverse transcriptase. These techniques have generated several cDNA fragments corresponding to the pol region of the MDS associated retrovirus. The present invention relates to the cDNAs corresponding to the pol region of the MDS associated virus and their use in diagnostic and prognostic evaluations.

The present invention relates to isolated preparations of a novel retrovirus associated with MDS and acute leukemia, herein referred to as "MDS associated retrovirus." The present invention relates to isolated genome of the novel retrovirus and the nucleotide and the nucleic acid molecules encoding said genome. The present invention relates to nucleotide sequences that encompass portions or fragments of the MDS associated retroviral nucleotides which can be utilized as probes or primers in the methods of the invention for identifying and diagnosing individuals at a risk for or exhibiting MDS and acute leukemia.

The present invention encompasses methods for the diagnostic evaluation, and prognostic evaluation of MDS associated retroviral infection and associated disorders including MDS and acute leukemia, wherein such methods comprise utilizing the nucleic acid molecules of the present invention to measure levels of MDS associated retroviral nucleotide sequences.

The present invention further provides for diagnostic kits for the practice of such methods. In one embodiment, the kit is made up of instructions for carrying out any of the methods described herein. The instructions can be provided in any intelligible form through a tangible medium, such as printed on paper, computer readable media, or the like. The present kits can also include one or more reagents, buffers, culture media, culture media supplements, chromatic or fluorescent dyes for staining or labeling a specific target, radioactive isotopes for labeling a specific target, and/or disposable lab equipment, such as multi-well plates in order to readily facilitate implementation of the present methods.

The present invention relates to therapeutic methods and compositions for treatment and prevention of diseases and disorders related to the infection with the MDS associated retrovirus and/or presence of the MDS associated retroviral activity and nucleotide sequences, including but not limited to, MDS and acute leukemias. The therapeutic methods and compositions are designed to target the MDS associated retroviral activity, such as anti-viral agents, and retroviral nucleotides, such as antisense molecules, and ribozymes. The therapeutic methods and compositions of the present invention are also designed to target the MDS associated retroviral gene products, including small molecules, large molecules and antibodies. In particular, the present invention encompasses the use of the isolated MDS associated retrovirus, associated retroviral activity and retroviral gene products to generate antibodies for the detection of the MDS associated retrovirus in tissue samples in diagnostic protocols and/or for formulation into vaccine preparations for the treatment and/or prevention of MDS associated retrovirus infection and related disorders, MDS and acute leukemias.

Identification and Isolation Of MDS Associated Retrovirus 5.1.1 Culturing Cells Infected with the MDS Associated Retrovirus The present invention relates to a retrovirus associated with MDS. The MDS associated retrovirus of the invention may be isolated from bone marrow hematopoietic cells such as stromal or parenchymal hematopoietic cells.

In order to establish bone marrow cultures containing the MDS associated in accordance, the following protocol can be used. Bone marrow core biopsy samples are obtained with informed consent from patients afflicted with MDS. Prior to culture, under sterile conditions, the biopsy piece is washed with Hank's saline, is dissected longitudinally and transversely followed by gentle teasing into minute fragments which are distributed in 35×10 mm petri dishes.

To all petri dishes, 1 ml of culture medium comprising RPMI 1640 with 12.5% horse serum, 12% fetal bovine serum, 20.0 mM L-glutamine, $10^{-4}M$ b-mercapatoethanol, $10^{-6}M$ hydrocortisone, 200 units/ml penicillin and streptomycin is added. Neither additional growth factors nor cytokines are added to the culture medium. Cultures are maintained at 37° C. in a humidified 5% CO2-in-air environment with replacement of half of the growth medium including non adherent cells with an equal volume of fresh medium weekly. When cultures reach approximately 80% to 100% confluence, between 8 to 22 weeks, they are treated with 0.25% trypsin and fixed.

In order to establish adherent layers of cell cultures infected with MDS associated retrovirus from bone marrow biopsies, the following protocol can be used. Primary bone marrow biopsy sample is teased and simultaneously cultured in complete medium without any cytokines or growth factors on approximately 6 plates per sample at 37° C. in a humidified 5% CO2 chamber for 8 to 22 weeks. All of the plates are weekly examined under phase contrast microscopy before half of the supernatant medium is replaced with fresh medium. The non adherent cells in the harvested medium are counted for viability and logged routinely.

The biopsy pieces should latch onto the culture plate in the first week, followed by the generation of stromal layer with the stem cells and maturing mycloid cells being released into the growth medium. By week 4, the plates are 30% to 40% confluent with bipolar, tripolar or multipolar monolayer and adipocytes. By week 8 to week 10, the plates are 80% to 100% confluent with compact parallel multiple layers of fibroblasts, macrophage and adipocytes. Also, preadipocytes and some adipocytes may be routinely observed in close proximity of the bone pieces over the monolayer. Cells in the area close to the bone may achieve contact inhibition of growth before peripheral cells, and the morphology may appear epithelial like under a phase contrast microscope. The plates are sacrificed once they reach 80% to 100% confluence.

The present invention relates to cell cultures infected with MDS associated retrovirus generated in accordance with the present invention. In particular, the present invention relates to cell cultures infected with MDS associated retrovirus obtained from a female patient afflicted with DMS, RAZA I/2000, which have been deposited with the ATCC. The Applicants have also deposited with the ATCC, cell cultures obtained from bone marrow biopsies from patients which are not afflicted with MDS, RAZA II/2000, which do not contain reverse transcriptase activity nor do they contain MDS associated retrovirus.

The present invention relates to cell cultures infected with MDS associated retrovirus generated from primary bone marrow biopsy cultures obtained from patients afflicted with MDS. The present invention further relates to cell cultures infected with MDS associated retrovirus generated from primary hematopoietic cell cultures obtained from patients afflicted with MDS.

The present invention further relates to primary cell cultures or transformed cells or cell lines which are infected with MDS associated retrovirus following co-culture with primary cell cultures obtained from patients afflicted with MDS. In particular, the present invention relates to primary cell cultures or transformed cells or cell lines which are infected with MDS associated virus following co-culture with MDS associated retrovirus infected cells, RAZA I/2000.

The present invention further relates to primary cell cultures or transformed cells or cell lines which are infected with MDS associated retrovirus following co-culture with isolated or cell-free preparations of MDS associated retrovirus. In particular, the present invention relates to primary cell cultures, transformed cells or cell lines which are infected with MDS associated retrovirus following co-culture with isolated or cell-free preparations of MDS associated virus isolated from RAZA I/2000 cells.

5.1.2 Isolation of MDS Associated Retrovirus

The present invention relates to isolated or cell free preparations of the MDS associated retrovirus. The present invention further relates to methods of isolating the MDS associated virus from primary cell cultures, transformed cells or cell lines which are infected with MDS associated retrovirus.

In an embodiment of the present invention, the MDS associated retrovirus may be isolated from bone marrow hematopoietic cells, such as stromal or parenchyma hematopoietic cells. In another embodiment of the invention, the MDS associated retrovirus may be isolated from lymphocytes, monocytes, bone marrow stem cells, fibroblasts, endothelial cells, or dentritic cells.

Bone marrow biopsies from MDS patients are grown in culture and stromal fibroblasts are subcultured. Culture supernatants are filtered and concentrated by centrifugation. The resulting pellet is assayed for reverse transcriptase activity as described in Section 6, infra.

The filtered culture supernatant which was positive for reverse transcriptase activity is layered on top of a linear sucrose density gradient solution and centrifuged. Fractions with the highest retroviral activity are collected and concentrated. MDS associated retrovirus may isolated by subsequent purification of the retroviral fractions using procedures known to those skilled in the art.

Purified virus, viral extracts or structural proteins, crude lysates and fractions of the MDS associated retrovirus are recognized by the sera of patients afflicted with MDS or other acute leukemias. Conversely, the MDS associated virus and/or the extracts, structural proteins, lysates thereof recognize the sera of patients afflicted with MDS. Accordingly, immunological reactions known in the art are used to detect antibodies that specifically bind to antigenic sites of the MDS associated retrovirus in samples of body fluids or cell cultures from patients with MDS. These immunological assays are described in greater detail in Section 6, infra.

MDS Associated Retroviral Nucleotides

The retroviral nucleotides of the present invention relate to the total RNA isolated from purified or cell-free preparations of MDS associated retrovirus. The retroviral nucleotides of the present invention relate to the total RNA isolated from purified or cell-free preparations of MDS associated virus which encode the viral genome or portions thereof.

The present invention also relates to nucleotide sequences of eight or more nucleotides in length which hybridize selectively to the RNA genome encoding the MDS associated virus, but do not hybridize under stringent conditions to the RNA genomes of HIV, HTLV-I or HTLV-II or MMTV.

The present invention relates to those nucleotide sequences which encode portions of the genome of the MDS associated retrovirus. In particular, the present invention relates to those nucleotide which encode the poi region, or portions thereof, of the MDS associated retrovirus. The RNA isolated from MDS associated retrovirus has been converted to cDNA using random primers corresponding to highly conserved poi regions of known retroviruses, MMTV, HTLV-1 and HIV and using reverse transcriptase. Said primers include:

| | | |
|---|---|---|
| rt1 | ACCATTCCTTTAGCTGCCCA | SEQ ID NO:1 |
| rt2 | GCCTTTACTATACCAGCCATA | SEQ ID NO:2 |
| rt3 | CCTTAGCTGAGCAAGACTGT | SEQ ID NO:3 |
| rt4 | CTTTCACTGTTCCAGCCCTT | SEQ ID NO:4 |
| rt5 | TCAACTCTGTCCTCTTCTGC | SEQ ID NO:5 |
| rt6 | CCTTCTCTGTGCCTTCTGTT | SEQ ID NO:6 |
| rt7 | WSHCCHTGGAAYACWCCHRTNTTYGT | SEQ ID NO:7 |
| rt8 | CARTGGAARGNTTTNCCNCARGGNATG | SEQ ID NO:8 |
| rt9 (ANTI) | WKRSYWCSWRGKAAWKGY | SEQ ID NO:9 |
| rt10 (ANTI) | AHDKKKTKKVWCAGYKARRG | SEQ ID NO:10 |
| rt11 (ANTI) | RYRRGAAGRSAYWCWRHWGR | SEQ ID NO:11 |
| rt12 | MNWRWRSWRRRYWTTSYANKG | SEQ ID NO:12 |
| 5' | RWRMAWRTCRTCCATRTAHTG-3' | SEQ ID NO:13 |
| 5' | RSAADGTDYTDCCNCARGG-3' | SEQ ID NO:14 |
| 5' | CCTYGNGGHARHACHTTSYA-3' | SEQ ID NO:15 |
| 5' | GTNTTYSYMRTNAARAARRMR-3' | SEQ ID NO:16 |

These techniques have generated several cDNA fragments corresponding to the pol region of the MDS associated retrovirus. The present invention relates to those nucleotide sequences corresponding to the pol region of the MDS associated virus and having less than 80% nucleotide sequence identity with those sequences of the pol region of MMTV, HTLV-1, and HIV. The present invention further relates to those nucleotide sequences corresponding to the pol region of the MDS associated virus with the proviso that the complement of said nucleotide sequences does not hybridize under highly stringent conditions to the nucleotide sequences of the pol region of MMTV, HIV, HTLV I or HTLV II.

The MDS associated retroviral nucleotide sequences of the present invention include: (a) nucleotide sequences and fragments thereof that encode a portion of the MDS associated retroviral genome of the present invention; (b) nucleotide sequences that comprise a MDS associated retroviral genome or a portion, mutant or allelic variant thereof; (c) nucleotide sequences comprising the novel retroviral sequences disclosed herein that encode retroviral gene products, as well as fragments thereof; and (d) nucleotide sequences (e.g., primers) or a portion thereof, which can be utilized as part of the methods of the invention for identifying and diagnosing individuals at a risk for exhibiting MDS and acute leukemias.

The MDS associated retroviral nucleotide sequences of the invention further include: (a) any nucleotide sequence that hybridizes to the complement of a nucleic acid molecule that encodes a MDS associated retroviral gene product under highly stringent conditions, e.g., hybridization to filter-bound DNA in 0.5 M NaHPO4, 7% sodium dodecyl sulfate (SDS), 1 mM EDTA at 65° C., and washing in 0.1×SSC/ 0.1% SDS at 68° C. (Ausubel F. M. et al., eds., 1989, Current Protocols in *Molecular Biology*, Vol. I, Green Publishing Associates, Inc., and John Wiley & sons, Inc., New York, at p. 2.10.3). In a preferred embodiment, such nucleic acid molecules encode gene products functionally equivalent to a MDS associated retroviral gene product; and any nucleotide sequence that hybridizes to the complement of a nucleic acid molecule that encodes a MDS associated retroviral gene product under less stringent conditions, such as moderately stringent conditions, e.g., washing in 0.2×SSC/0.1% SDS at 42° C. (Ausubel et al., 1989, supra), and which encodes a functionally equivalent MDS associated retroviral gene product. Functional equivalents of MDS associated retroviral nucleotides include naturally occurring MDS associated retroviral nucleic acid molecules present in the same or different species.

Among the nucleic acid molecules of the invention are deoxyoligonucleotides ("oligos") which hybridize under highly or moderately stringent conditions to the MDS associated retroviral nucleic acid molecules described above. Exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as antisense molecules, useful, for example, in MDS associated retroviral gene regulation, and/or as antisense primers in amplification reactions of MDS associated retroviral gene nucleic acid sequences. Further, such sequences may be used as part of ribozyme and/or triple helix sequences, also useful for MDS associated retroviral gene regulation. Still further, such molecules may be used as components of diagnostic methods whereby, for example, the presence of a particular MDS associated retroviral nucleic acid molecules involved in a disorder, such as MDS and chronic leukemias, may be detected.

Fragments of the MDS associated retroviral nucleic acid molecules can be at least 10 nucleotides in length. In alternative embodiments, the fragments can be about 20, 30, 40, 50, 60, 70, 80, 90, 100, 200, 300, 400, 500, 1000, or more nucleotides in length. Alternatively, the fragments can comprise sequences that encode at least 10, 20, 30, 40, 50, 100, or more continuous amino acid residues of the MDS associated retroviral gene products.

The MDS associated retroviral nucleotide sequences of the invention can be readily obtained, for example, by standard sequencing and the sequence provided herein.

With respect to the cloning of additional allelic variants of the MDS associated retroviral genome gene and homologues from other species (e.g., mouse), the isolated MDS associated retroviral gene sequences disclosed herein may be labeled and used to screen a cDNA library constructed from mRNA obtained from appropriate cells or tissues (e.g., bone marrow or hematopoietic tissues) derived from the organism (e.g., guinea pig, bovine, and mouse) of interest. The hybridization conditions used should generally be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, a MDS associated retroviral genome allelic variant may be isolated from, for example, human nucleic acid, by performing PCR using two degenerate oligonucleotide primer pools designed on the basis of nucleotide sequences disclosed herein. The template for the reaction may be cDNA obtained by reverse transcription of mRNA prepared from, for example, human or non-human cell lines or tissue known or suspected to express a retroviral genome allele (such as, for example, bone marrow tissue from individuals having MDS and acute leukemias).

The PCR product may be subcloned and sequenced to ensure that the amplified sequences represent the sequences of a MDS associated retroviral genome nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology and rapid amplification of cDNA ends (RACE) may also be utilized to isolate full length cDNA sequences. In particular the nucleic acids of the present invention may be used to isolate the MDS associated viral genome from patients' samples, infected bone marrow cells, or by screening a full representation of MDS bone marrow cDNA libraries.

In accordance with the present invention, upon identification of retroviral genomic nucleic acid molecules, the presence of retroviral particles may be determined using routine protocols known to those skilled in the art, e.g., co-culture hematopoietic tissue samples from MDS patients with cultured cells including but not limited to: cord blood cells, human lymphocytes, human foreskin fibroblasts, and human placental tissue and subsequently detect retroviral infection of the cultured cells. Also in accordance with the present invention, cells including but not limited to normal lymphocytes, epithelial U293 cells, CHO cells, BHK cells, COS cells, regular 293 cells, 3T3 cells, or U138 cells can be stimulated by phytohem-agluttanin (PHC), cytokines or growth factors and be receptive to retroviral infection. The presence of retroviral particles in these cultured cells may be determined using routine protocols known in the art. Evidence for retroviral infection may be determined by RT-PCR, cell morphology, electron microcopy, and Western blot of bone marrow extracts or cultures of primary hematopoietic tissue samples.

Further, in accordance with the present invention, RNA may be isolated, following standard procedures, from an appropriate cellular or tissue source (i.e., one known, or suspected, to express the MDS associated retroviral genome, such as, for example, bone marrow tissue samples obtained through biopsy or post-mortem from a subject with MDS). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, supra.

A cDNA of a mutant allelic variant of the MDS associated retroviral genome may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant MDS associated retroviral allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant MDS associated retroviral allele to that of the normal MDS retroviral allele, the mutation(s) responsible for the loss or alteration of function of the mutant MDS associated retroviral gene product can be ascertained.

Alternatively, a genomic library can be constructed using DNA obtained from an individual suspected of or known to carry a mutant MDS associated retroviral allele, or a cDNA library can be constructed using RNA from a tissue known, or suspected, to express a mutant MDS associated retroviral allele. An unimpaired MDS associated retroviral genome or any suitable fragment thereof may then be labeled and used as a probe to identify the corresponding mutant MDS associated retroviral allele in such libraries. Clones containing the mutant MDS associated retroviral sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant MDS associated retroviral allele in an individual suspected of or known to carry such a mutant allele. In this manner, gene products made by the putatively mutant tissue may be expressed and screened using standard antibody screening techniques in conjunction with antibodies raised against the normal MDS associated retroviral gene product, as described, below, in Section 5.3. (For screening techniques, see, for example, Harlow and Lane, eds., 1988, "Antibodies: A Laboratory Manual," Cold Spring Harbor Press, Cold Spring Harbor.)

The invention also includes nucleic acid molecules, preferably DNA molecules, that are the complements of the nucleotide sequences of the preceding paragraphs.

Protein Products of the MDS Associated Retroviral Genome

MDS associated retroviral gene products, or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of disorders, such as MDS and acute leukemias.

In addition, MDS associated retroviral genome products may include proteins that represent functionally equivalent gene products. Functionally equivalent gene products may include, for example, gene products encoded by one of the MDS associated retroviral nucleic acid molecules described in Section 5.2, above. In preferred embodiments, such functionally equivalent MDS associated retroviral gene products are naturally occurring gene products. Such an equivalent MDS associated retroviral gene product may contain deletions, including internal deletions, additions, including additions yielding fusion proteins, or substitutions of amino acid residues within and/or adjacent to the amino acid sequence encoded by the MDS associated retroviral gene sequences described, above, in Section 5.2, but that result in a "silent" change, in that the change produces a MDS associated retroviral gene product with the same activity.

Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Antibodies to MDS Associated Retroviral Gene Products

Described herein are methods for the production of antibodies capable of specifically recognizing MDS associated retrovirus or one or more MDS associated retroviral gene product epitopes or epitopes of conserved variants or peptide fragments of the MDS associated retroviral gene products. Further, antibodies that specifically recognize mutant forms of MDS associated retroviral, are encompassed by the invention.

The present invention relates to extracts of the MDS associated retrovirus that can be recognized immunologically from patients afflicted with MDS and whose bone marrow biopsy cultures indicate a reverse transcriptase activity. Any type of immunological assay may be employed, in particular immunofluorescence, immunoenzymatic or radioimmunoprecipitation are examples of the types of assays which may be employed in connection with the present invention.

Such antibodies or sera capable of specifically recognizing MDS associated retrovirus or epitope thereof may include, but are not limited to, polyclonal antibodies, monoclonal antibodies (mAbs), humanized or chimeric antibodies, single chain antibodies, Fab fragments, F(ab')2 fragments, fragments produced by a Fab expression library, anti-idiotypic (anti-Id) antibodies, and epitope-binding fragments of any of the above, including the polyclonal and monoclonal antibodies. Such antibodies may be used, for example, in the detection of a MDS associated retroviral gene product in an biological sample and may, therefore, be utilized as part of a diagnostic or prognostic technique whereby patients may be tested for abnormal levels of MDS associated retroviral gene products, and/or for the presence of abnormal forms of such gene products. Such antibodies may also be utilized in conjunction with, for example, compound screening schemes, for the evaluation of the effect of test compounds on MDS associated retroviral gene product levels and/or activity. Additionally, such antibodies can be used in conjunction with the gene therapy techniques described below, to evaluate the normal and/or engineered MDS associated retroviral genome expressing cells prior to their introduction into the patient.

Anti-MDS associated retroviral gene product antibodies may additionally be used in pharmaceutical formulations and used in methods for the treatment and/or prevention of MDS associated retroviral infection and associated disorders MDS and chronic leukemias.

For the production of antibodies against a MDS associated retroviral gene product or a MDS associated retrovirus various host animals may be immunized by injection with a MDS associated retroviral gene product or MDS associated retroviral particles. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*.

Polyclonal antibodies are heterogeneous populations of antibody molecules derived from the sera of animals immunized with an antigen, or an antigenic functional derivative thereof. For the production of polyclonal antibodies, host animals such as those described above, may be immunized by injection with MDS associated retroviral gene product or viral particles supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, *Nature* 256:495–497; and U.S. Pat. No. 4,376,110), the human B-cell hybridoma technique (Kosbor et al., 1983, *Immunology Today* 4:72; Cole et al., 1983, *Proc Natl Acad Sci USA* 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, *Proc Natl Acad Sci* 81:6851–6855; Neuberger, et al., 1984, *Nature* 312:604–608; Takeda, et al., 1985, *Nature* 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest," Kabat, E. et al., U.S. Department of Health and Human Services (1983)). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, *Science* 242:423–426; Huston, et al., 1988, *Proc Natl Acad Sci USA* 85:5879–5883; and Ward, et al., 1989, *Nature* 334:544–546) can be adapted to produce single chain antibodies against MDS associated retroviral particles and MDS associated retroviral gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')2 fragments, which can be produced by pepsin digestion of the antibody molecule and the Fab fragments, which can be generated by reducing the disulfide bridges of the F(ab')2 fragments. Alternatively, Fab expression libraries may be constructed (Huse, et al., 1989, Science 246:1275–1281) to allow rapid and easy identification of monoclonal Fab fragments with the desired specificity.

Uses of MDS Associated Retroviral Gene Sequences Gene Products, and Antibodies

Described herein are various applications of isolated MDS associated retroviral particles, gene sequences, MDS associated retroviral gene products, including peptide fragments and fusion proteins thereof, and of antibodies directed against MDS associated retroviral gene products and peptide fragments thereof. Such applications include, for example, characterization of the complete genome of the MDS associated retrovirus; identification and characterization of novel retroviruses, prognostic and diagnostic evaluation of an infection by MDS associated retrovirus or associated disorders, MDS and chronic leukemias, and the identification of subjects with a predisposition to such disorders.

Additionally, such applications include methods for the treatment of infection by MDS associated retrovirus or associated disorders, MDS and chronic leukemias, as described below and for the identification of compounds that modulate the expression of the MDS associated retroviral gene and/or the synthesis or activity of the MDS associated retroviral gene product.

Diagnosis of MDS Associated Retrovirus and Related Disorders

A variety of methods can be employed for the diagnostic and prognostic evaluation of MDS associated retrovirus infection and related disorders MDS and chronic leukemias and for the identification of subjects having a predisposition to such disorders.

Such methods may, for example, utilize reagents such as the MDS associated retroviral gene nucleotide sequences described in Sections 5.2, and antibodies directed against MDS associated retroviral gene products, including peptide fragments thereof, as described, above, in Section 5.3. Specifically, such reagents may be used, for example, for:
(1) the detection of the presence of MDS associated retroviral nucleotide sequences;
(2) the detection of presence of MDS associated retroviral gene product.

The detection methods of the present invention can be utilized in pharmacogenetic methods to monitor and to optimize therapeutic drug treatments.

The methods described herein may be performed, for example, by utilizing pre-packaged diagnostic kits comprising at least one specific MDS associated retroviral nucleic acid or anti-MDS associated retroviral gene product antibody reagent described herein, which may be conveniently used, e.g., in clinical settings, to diagnose patients exhibiting MDS and chronic leukemias and infection by the MDS associated retrovirus.

5.6.1 Prognosis of MDS Associated Retrovirus Infection

In another embodiment, the detection methods described above can be employed for the prognostic evaluation of MDS associated retrovirus infection. The detection of MDS associated retrovirus or fragments thereof can be indicative of a predisposition to MDS and related disorders as well as other cancers. The detection methods described above can be used as prognostic tools for determining a predisposition to any cancer, including cancer that has metastasized to multiple sites or leukemic cancers that circulate in blood, lymph or other body fluids or cancers of solid tumor tissue.

Using the methods of the invention, an embodiment of the invention encompasses the detection of MDS associated retrovirus in cancer cells including, but not limited to: tumor cells, including, but not limited to, for example, tumors that are mesenchymal in origin (sarcomas), i.e., fibrosarcomas; myxosarcomas; liposarcomas; chondrosarcomas; osteogenic sarcomas; angiosarcomas; endotheliosarcomas; lymphangiosarcomas; synoviosarcomas; mesotheliosarcomas; Ewing's tumors; myelogenous leukemias; monocytic leukemias; malignant lymphomas; lymphocytic leukemias; plasmacytomas; leiomyosarcomas and rhabdomyosarcoma. In addition, it is contemplated that the detection methods can be used in the prognostic evaluation of tumor cells from tumors that are epithelial in origin (carcinomas), i.e., squamous cell or epidermal carcinomas; basal cell carcinomas; sweat gland carcinomas; sebaceous gland carcinomas; adenocarcinomas; papillary carcinomas; papillary adenocarcinomas; cystadenocarcinomas; medullary carcinomas; undifferentiated carcinomas (simplex carcinomas); bronchogenic carcinomas; bronchial carcinomas; melanocarcinomas; renal cell carcinomas; hepatocellular carcinomas; bile duct carcinomas; papillary carcinomas; transitional cell carcinomas; squamous cell carcinomas; choriocarcinomas; seminomas; embryonal carcinomas malignant teratomas and teratocarcinomas. The MDS associated retrovirus detection methods can also be used to evaluate cells of leukemia, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. It is also contemplated that the MDS associated retrovirus might be detected in tumor cells from tumors induced by chemical carcinogens or radiation. Chemical carcinogens include carcinogens associated with cigarette smoking, such as hydrocarbons and carcinogenic air, food, cosmetics or other pollutants.

Detection of MDS Associated Retroviral Nucleic Acid Molecules

A variety of methods can be employed to screen for the presence of MDS associated retroviral to detect and/or assay levels of MDS associated retroviral nucleic acid sequences.

MDS associated retroviral nucleic acid sequences may be used in hybridization or amplification assays of biological samples to detect levels and abnormalities involving MDS associated retroviral genome structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of MDS associated retroviral gene-specific mutations can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such as described in Section 5.2, above, under conditions favorable for the specific annealing of these reagents to their complementary sequences within or flanking the MDS associated retroviral genome. The diagnostic methods of the present invention further encompass contacting and incubating nucleic acids for the detection of single nucleotide mutations or polymorphisms of the MDS associated retroviral genome.

After incubation, all non-annealed nucleic acids are removed from the nucleic acid: MDS associated retroviral molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.2 are easily removed. Detection of the remaining, annealed, labeled MDS associated retroviral nucleic acid reagents is accomplished using standard techniques well-known to those in the art. The MDS associated retroviral gene sequences to which the nucleic acid reagents have annealed can be compared to the annealing pattern expected from a normal MDS associated retroviral gene sequence in order to determine whether a MDS associated retroviral gene mutation is present.

In a preferred embodiment, MDS associated retroviral mutations or polymorphisms can be detected by using a microassay of MDS associated retroviral nucleic acid sequences immobilized to a substrate or "gene chip" (see, e.g. Cronin, et al., 1996, *Human Mutation* 7:244–255).

Alternative diagnostic methods for the detection of MDS associated retroviral gene specific nucleic acid molecules, in patient samples or other appropriate cell sources, may involve their amplification, e.g., by PCR (the experimental embodiment set forth in Mullis, 1987, U.S. Pat. No. 4,683, 202), followed by the analysis of the amplified molecules using techniques well known to those of skill in the art, such as, for example, those listed above.

Those MDS associated retroviral nucleic acid sequences which are preferred for such amplification-related diagnostic screening analyses are oligonucleotide primers which are described in the Working Examples herein.

Additional MDS associated retroviral nucleic acid sequences which are preferred for such amplification-related analyses are those which will detect the presence of an MDS associated retroviral polymorphism. Such polymorphisms include ones which represent mutations associated with an MDS associated retroviral-mediated disorders.

Additionally, well-known genotyping techniques can be performed to identify individuals carrying MDS associated retroviral gene mutations. Such techniques include, for example, the use of restriction fragment length polymorphisms (RFLPs), which involve sequence variations in one of the recognition sites for the specific restriction enzyme used.

Further, improved methods for analyzing DNA polymorphisms, which can be utilized for the identification of MDS associated retroviral gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the MDS associated retroviral gene, and the diagnosis of diseases and disorders related to MDS associated retroviral mutations.

Also, Caskey et al. (U.S. Pat. No. 5,364,759) describe a DNA profiling assay for detecting short tri and tetra nucleotide repeat sequences. The process includes extracting the DNA of interest, such as the MDS associated retroviral gene, amplifying the extracted DNA, and labeling the repeat sequences to form a genotypic map of the individual's DNA.

Other methods well known in the art may be used to identify single nucleotide polymorphisms (SNPs), including biallelic SNPs or biallelic markers which have two alleles, both of which are present at a fairly high frequency in a population. Conventional techniques for detecting SNPs include, e.g., conventional dot blot analysis, single stranded conformational polymorphism (SSCP) analysis (see, e.g., Orita et al., 1989, *Proc Natl Acad Sci USA* 86:2766–2770), denaturing gradient gel electrophoresis (DGGE), heteroduplex analysis, mismatch cleavage detection, and other routine techniques well known in the art (see, e.g., Sheffield et al., 1989, *Proc Natl Acad Sci* 86:5855–5892; Grompe, 1993, *Nature Genetics* 5:111–117). Alternative, preferred methods of detecting and mapping SNPs involve micro sequencing techniques wherein an SNP site in a target DNA is detecting by a single nucleotide primer extension reaction (see, e.g., Goelet et al., PCT Publication No. WO92/15712; Mundy, U.S. Pat. No. 4,656,127; Vary and Diamond, U.S. Pat. No. 4,851,331; Cohen et al., PCT Publication No. WO91/02087; Chee et al., PCT Publication No. WO95/11995; Landegren et al., 1988, *Science* 241:1077–1080; Nicerson et al., 1990, *Proc Natl Acad Sci USA* 87:8923–8927; Pastinen et al., 1997, *Genome Res* 7:606–614; Pastinen et al., 1996, *Clin Chem* 42:1391–1397; Jalanko et al., 1992, *Clin Chem* 38:39–43; Shumaker et al., 1996, *Hum Mutation* 7:346–354; Caskey et al., PCT Publication No. WO 95/00669).

The level of MDS associated retroviral gene expression can also be assayed. For example, RNA from a cell type or tissue known, or suspected, to express the MDS associated retroviral gene, such as primary bone marrow biopsy or hematopoietic tissue sample, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the MDS associated retroviral gene. Such analyses may reveal both quantitative and qualitative aspects of the expression pattern of the MDS associated retroviral gene, including activation or inactivation of MDS associated retroviral gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the MDS associated retroviral gene nucleic acid reagents described in Section 5.2. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such MDS associated retroviral gene expression assays "in situ," i.e., directly upon tissue sections (fixed and/or frozen) of patient tissue obtained from biopsies or resections, such that no nucleic acid purification is necessary. Nucleic acid reagents such as those described in Section 5.2 may be used as probes and/or primers for such in situ procedures (see, for example, Nuovo, G. J., 1992, "PCR In Situ Hybridization: Protocols And Applications," Raven Press, NY).

Alternatively, if a sufficient quantity of the appropriate cells can be obtained, standard Northern analysis can be performed to determine the level of mRNA expression of the MDS associated retroviral gene.

Methods of Treating MDS and Associated Disorders

In another embodiment of the present invention, various therapeutic measures are used in combination to produce desired benefits. Transplantation is a successful curative therapy but remains an option for less than 5% of all patients. Standard treatment of MDS has included supportive care. Palliative measures are directed at inducing differentiation (vitamins), hyper-proliferation (growth factors), and cell kill (chemotherapy). Growth factors Neupogen and Epogen have been administered to increase the proliferation of WBCs and red cells in the marrow. Other therapeutic strategies are directed at reducing the cytokine-induced death of hematopoietic cells either by neutralizing the cytokine directly (TNF receptor Enbrel), or indirectly (pentoxifyline, amifostine, thalidomide) or eliminating the cells producing the cytokines (cyclosporin, anti-thymocyte globulin or ATG). Because the master switch which controls a whole cascade of cytokines is Tumor Necrosis Factor (TNF), numerous therapeutic agents have been designed to neutralize TNF activity. In a preferred embodiment, these therapeutic strategies are combined with other therapeutic approaches (e.g., anti-retroviral based) discussed below.

5.8.1 Anti-Retroviral Inhibitory Approaches

In another embodiment, anti-retroviral therapeutic agents are administered alone or in combination or in conjunction with other therapeutic approaches. Such anti-retroviral agents include but are not limited to antivirals, such as cytokines, e.g., rIFN α, rIFN β, rIFN γ; inhibitors of reverse transcriptase including but not limited to nucleoside reverse transcriptase inhibitors (NRTIs) e.g., Zidovudine, (AZT and ZDV), Lamivudine (3TC), Stavudine (D4T), Didanosine (ddI), Zalcitabine (ddC), Abacavir (ABC) and other dideoxynucleosides or dideoxyfluoronucleosides; non-nucleoside reverse transcriptase inhibitors (NNRTIs) e.g., Nevirapine, Delavirdine, and Efavirenz; protease inhibitors, e.g., Indinavir, Ritonavir, Saquinavir, Nelfinavir, and Amprenavir; nucleotide reverse transcriptase inhibitors, e.g., Adefovir; inhibitors of viral mRNA capping, such as ribavirin; other inhibitors of viral protease, such as ABT-538 and MK-639; amphotericin B, which is a lipid-binding molecule known to have anti-viral activity; and castanospermine as an inhibitor of glycoprotein processing.

Other anti-retroviral agents identified included but are not limited to: BW935U83; second generation NNRTI drug candidate DPC 963; thymidylate synthase; inosinate dehydrogenase; cytidine-5'-triphosphate synthetase and other enzymes from the de novo nucleotide biosynthesis pathway which potentiate the antiviral action of NRTIs; PMPA; tenofovir; hydroxyurea; racemic dOTC (BCH-10652); N-acetylcysteine, glutathione; alpha-lipoic acid disubstituted alkyne; DPC 961; adefovir dipivoxil (ADV); quinoxaline non-nucleoside reverse transcriptase inhibitor, GW420867X; emivirine; analogs of Efavirenz (SUSTIVA); HBY-097; and Adefovir dipivoxil which is an ester prodrug of the nucleoside reverse transcriptase inhibitor adefovir (PMEA). In addition, halogenated nucleoside derivatives may be used as anti-viral agents, preferably 2',3'-dideoxy-2'-fluoronucleosides including, but not limited to, 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; and 2',3'-dideoxy-2',3'-didehydro-2'-fluoronucleosides including, but not limited to 2',3'-dideoxy-2',3'-didehydro-2'-fluorothymidine (Fd4T).

In another embodiment of the invention, a topoisomerase I inhibitor, an inhibitor of viral replication, may be used in combination with other therapeutic agents to enhance the antiviral affect achieved. Examples of topoisomerase inhibitors include but are not limited to: CPT-11 topotecan; 9-AC; GG-211; camptothecins and analogs thereof. A topoisomerase I inhibitor can be used in combination with anti-retroviral agents such as the nucleoside derivatives. Such combinations allow one to use a lower dose of the antiviral agent thus reducing the toxicity associated with that agent, without loss of antiviral activity because of the use of the topoisomerase I inhibitor. Moreover, such a combination also reduces or avoids viral resistance.

According to the present invention, topoisomerase I inhibitors can also be used in combination with uridine phosphorylase inhibitors, including but not limited to acyclouridine compounds, including benzylacyclouridine (BAU); benzyloxybenzylacyclouridine (BBAU); aminomethyl-benzylacyclouridine (AMBAU); aminomethyl-benzyloxybenzylacyclouridine (AMB-BAU); hydroxymethyl-benzylacyclouridine (HMBAU); and hydroxymethyl-benzyloxybenzylacyclouridine (HMBBAU).

Combinations of topoisomerase I inhibitors with the antiviral therapeutics described above may be tested for antiviral activity according to methods known in the art.

5.8.2 Inhibitory Antisense, Ribozyme and Triple Helix Approaches

In another embodiment, symptoms of MDS associated retroviral-mediated disorders may be ameliorated by decreasing the level of MDS associated retroviral gene expression and/or MDS associated retroviral gene product activity by using MDS associated retroviral gene sequences in conjunction with well-known antisense, gene "knock-out," ribozyme and/or triple helix methods to decrease the level of MDS associated retroviral gene expression. Among the compounds that may exhibit the ability to modulate the activity, expression or synthesis of the MDS associated retroviral gene, including the ability to ameliorate the symptoms of a MDS associated retroviral-mediated disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the MDS associated retroviral gene could be used in an antisense approach to inhibit translation of endogenous MDS associated retroviral mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, *Proc Natl Acad Sci USA* 86:6553–6556; Lemaitre, et al., 1987, *Proc Natl Acad Sci USA* 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, *BioTechniques* 6:958–976) or intercalating agents (see, e.g., Zon, 1988, *Pharm Res* 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5¢-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, *Nucl Acids Res* 15:6625–6641). The oligonucleotide is a 2¢-0-methylribonucleotide (Inoue, et al., 1987, *Nucl Acids Res* 15:6131–6148), or a chimeric RNA-DNA analogue (Inoue, et al., 1987, *FEBS Lett* 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, *Nucl Acids Res* 16:3209), methylphosphonate oligonucleotides can be prepared by use of controlled pore glass polymer supports (Sarin, et al., 1988, *Proc Natl Acad Sci USA* 85:7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, *Nature* 290:304–310), the promoter contained in the 3¢ long terminal repeat of Rous sarcoma virus (Yamamoto, et al., 1980, *Cell* 22:787–797), the herpes thymidine kinase promoter (Wagner, et al., 1981, *Proc Natl Acad Sci USA* 78:1441–1445), the regulatory sequences of the metallothionein gene (Brinster, et al., 1982, *Nature* 296:39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, *Science* 247, 1222–1225).

Ribozymes are enzymatic RNA molecules capable of catalyzing the specific cleavage of RNA. (For a review, see Rossi, 1994, *Current Biology* 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

Figure 4:
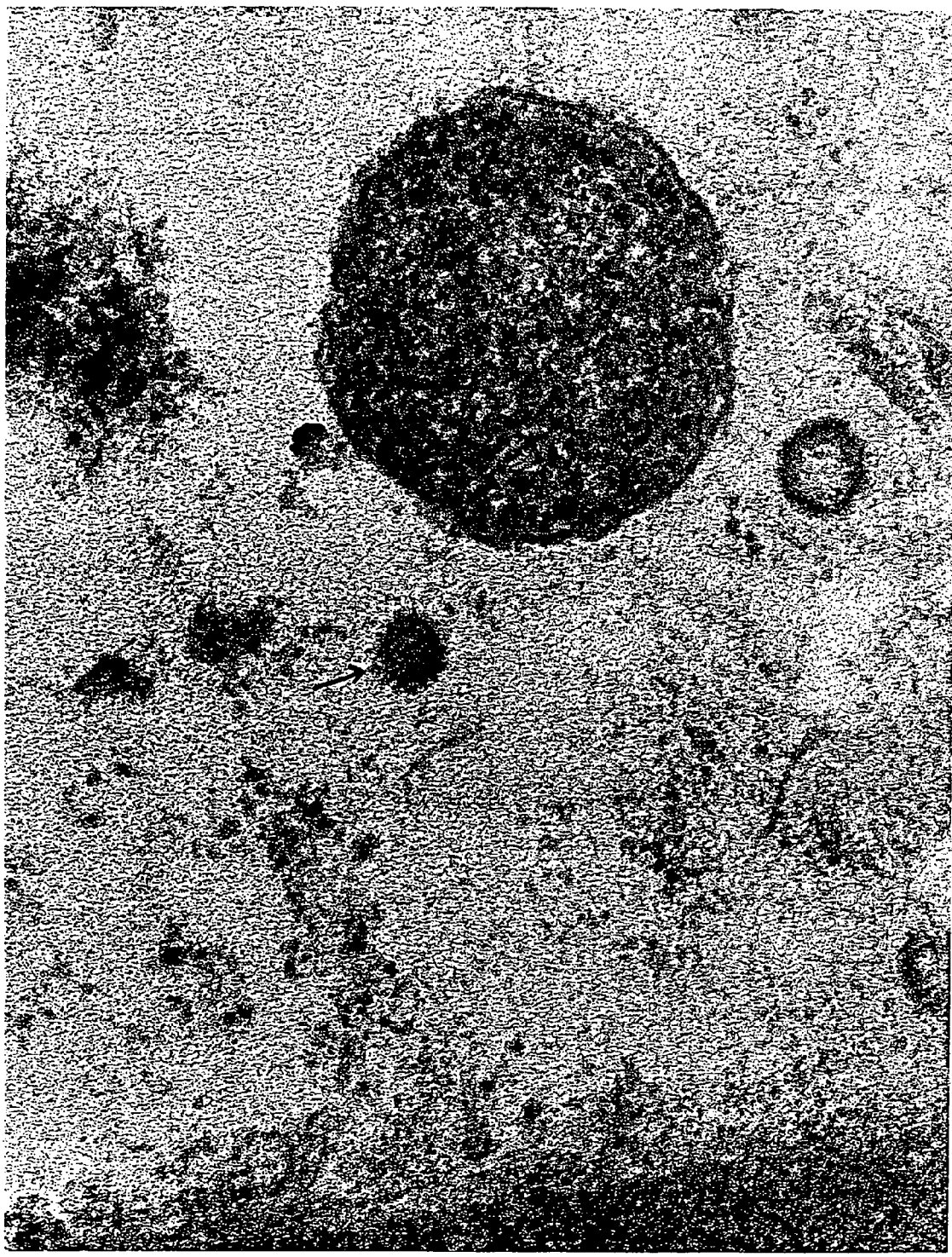
FIG. 4 shows a VLP in an MDS BM biopsy.
Figure 5:
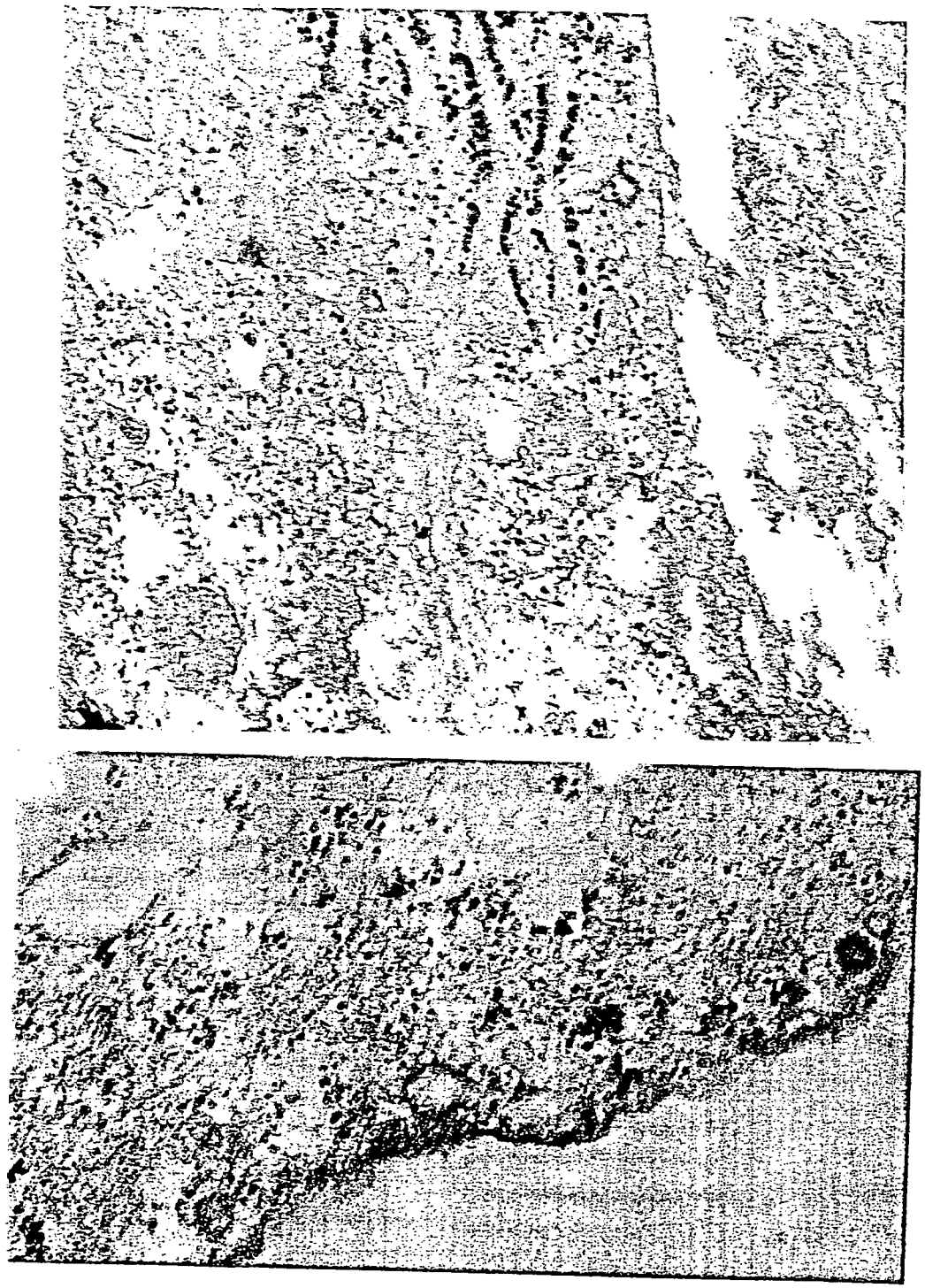
FIG. 5 shows a VLP seen in the cultured BM biopsy plate of an MDS patient positive for the reverse transcriptase assay.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, Molecular Biology and Biotechnology: A Comprehensive Desk Reference, VCH Publishers, New York, (see especially FIG. 4, page 833) and in Haseloff and Gerlach, 1988, Nature, 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in Tetrahymena thermophila (known as the IVS, or L-19 IVS RNA) and that has been extensively described by Thomas Cech and collaborators (Zaug, et al., 1984, *Science* 224:574–578; Zaug and Cech, 1986, *Science* 231:470–475; Zaug, et al., 1986, *Nature* 324:429–433; published International patent application No. WO 88/04300 by University Patents Inc.; Been and Cech, 1986, *Cell* 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, *Nature* 317:230–234; Thomas and Capecchi, 1987, *Cell* 51:503–512; Thompson, et al., 1989, *Cell* 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, *Anticancer Drug Des* 6(6):569–584; Helene, et al., 1992, *Ann NY Acad Sci* 660:27–36; and Maher, 1992, *Bioassays* 14(12):807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC+ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Pharmaceutical Preparations and Methods of Administration

The compounds that are determined to affect MDS associated retroviral gene expression or gene product activity can be administered to a patient at therapeutically effective doses to treat or ameliorate a MDS associated retroviral-mediated disorder. A therapeutically effective dose refers to that amount of the compound sufficient to result in amelioration of symptoms of such a disorder. Further, once a patient has been identified as being infected with the MDS associated retrovirus, antiviral therapy can be used to prevent the onset of MDS associated retroviral-mediated disorders.

In another embodiment, the invention encompasses the identification of patients susceptible to or at risk of MDS by detecting the presence of the MDS associated retrovirus. Further, the invention encompasses the treatment or prevention of MDS associated retroviral-mediated disorders comprising inhibiting or neutralizing infection by MDS-associated retrovirus.

5.9.1 Effective Dose

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.9.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, parenteral or mucosol (such as buccal, vaginal, rectal, sublingual) administration. In a preferred embodiment, local or systemic parenteral administration is used.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

Vaccine Formulations and Methods of Administration

The MDS associated virus in an attenuated form and MDS associated virus gene products have use in vaccine preparations and in immunoassays, e.g to detect or measure in a sample of body fluid from a vaccinated subject the presence of antibodies to the antigen, and thus to diagnose infection and/or to monitor immune response of the subject subsequent to vaccination.

The preparation of vaccines containing an immunogenic polypeptide as the active ingredient is known to one skilled in the art.

5.10.1 Determination of Vaccine Efficacy

The immunopotency of the MDS associated virus in an attenuated form and MDS associated virus gene products can be determined by monitoring the immune response in test animals following immunization with the antigen, or by use of any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

Methods of introducing the vaccine may include oral, intracerebral, intradermal, intramuscular, intraperitoneal, intravenous, subcutaneous, intranasal or any other standard routes of immunization. The immune response of the test subjects can be analyzed by various approaches such as: the reactivity of the resultant immune serum to the antigen, as assayed by known techniques, e.g., immunosorbant assay (ELISA), immunoblots, radioimmunoprecipitations, etc., or in the case where the antigen displays antigenicity or immunogenicity, by protection of the immunized host from infection by the MDS associated retrovinus and/or attenuation of symptoms due to infection in the immunized host.

As one example of suitable animal testing of a vaccine, the vaccine of the invention may be tested in rabbits for the ability to induce an antibody response to the antigen. Male specific-pathogen-free (SPF) young adult New Zealand White rabbits may be used. The test group each receives a fixed concentration of the vaccine. A control group receives an injection of 1 mM Tris-HCl pH 9.0 without the antigen.

Blood samples may be drawn from the rabbits every one or two weeks, and serum analyzed for antibodies to the viral protein. The presence of antibodies specific for the antigen may be assayed, e.g., using an ELISA.

5.10.2 Vaccine Formulations

Suitable preparations of such vaccines include injectables, either as liquid solutions or suspensions; solid forms suitable for solution in, suspension in, liquid prior to injection, may also be prepared. The preparation may also be emulsified, or the polypeptides encapsulated in liposomes. The active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

In one embodiment of the invention, recombinant vaccines may be formulated which express the MDS associated retroviral nucleic acid molecules of the present invention. In yet another embodiment, vaccines may be formulated which comprise the isolated MDS associated retrovirus which has been formulated using conventional techniques to "kill" or attenuate the virus. Such techniques include heat inactivation, or treatment with formalin, formaldehyde or β-propiolactone.

Examples of adjuvants which may be effective, include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine.

The effectiveness of an adjuvant may be determined by measuring the induction of antibodies directed against an immunogenic polypeptide containing a viral polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

The vaccine formulations of the invention comprise an effective immunizing amount of the viral protein and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Use of purified antigens as vaccine preparations can be carried out by standard methods. For example, the purified protein(s) should be adjusted to an appropriate concentration, formulated with any suitable vaccine adjuvant and packaged for use. Suitable adjuvants may include, but are not limited to: mineral gels, e.g., aluminum hydroxide; surface active substances such as lysolecithin, pluronic polyols; polyanions; peptides; oil emulsions; alum, and MDP. The immunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Effective doses (immunizing amounts) of the vaccines of the invention may also be extrapolated from dose-response curves derived from animal model test systems.

The invention also provides a pharmaceutical pack or kit comprising one or more containers comprising one or more of the ingredients of the vaccine formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

The present invention thus provides a method of immunizing an animal, or treating or preventing various diseases or disorders in an animal, comprising administering to the animal an effective immunizing dose of a vaccine of the present invention.

EXAMPLES

Identification and Isolation of a Novel Retrovirus in MDS Bone Marrow Culture 6.1.1 Preparation of MDS Bone Marrow Cultures Bone marrow core biopsy samples were obtained from MDS patients, and long term bone marrow cultures were established. Prior to culture, under sterile conditions, the biopsy piece was washed twice with Hank's saline, dissected longitudinally and transversely followed by gentle teasing into minute fragments which were distributed in six 35×10 mm petri dishes (nunc). One ml of culture medium, RPMI 1640 (GIBCO-BRL Life technologies) with 12.5% Horse Serum, 12.5% Fetal bovine Serum (GIBCO-BRL), 2.0 mM L-glutamine, 10-4 M b-mercaptoethanol, 10-6 M Hydrocortosone, 200 units/ml penicillin and streptomycin were added to all petri dishes (Dexter, 1979). Neither growth factors nor cytokines were added to the culture medium. Cultures were maintained at 37° C. in a humidified 5% $CO_2$-in-air environment with weekly replacement of half of the growth medium including non adherent cells with an equal volume of fresh medium. Cultures were 80%–100% confluent between 8 to 22 weeks.

Primary bone marrow biopsy samples were teased and simultaneously cultured in complete medium without any cytokines or growth factors on 6 plates per patient at 37° C. in a humidified 5% $CO_2$ chamber for 8–22 weeks. All the plates were weekly examined under phase contrast microscope before half of the supernatant medium was replaced with fresh medium. The non adherent cells in the harvested medium were counted for viability and logged routinely. The biopsy pieces latched onto the culture plate in the first week, followed by the generation of stromal layer with the stem cells and maturing myeloid cells being released into the growth medium. By week 4, plates were 30% to 50% confluent with bipolar, tripolar or multipolar monolayer and adipocytes, followed by 80%–100% confluency in 8th to 10th week with compact parallel multiple layers of fibroblasts, macrophages and adipocytes. Also preadipocytes and some adipocytes were routinely observed in close proximity of the bone pieces, over the monolayer. Cells in the area close to the bone achieved contact inhibition of growth before peripheral cells, and the morphology appeared epithelial like under the phase contrast microscope, while the giant adipocytes colonies were scattered across the plate.

6.1.2 Virus Isolation and Detection of Reverse Transcriptase Activity in MDS Bone Marrow Bone marrow biopsies were grown in culture, and stromal fibroblasts were expanded by subcultures as described above. Supernatants of the cultured stroma were filtered through 0.2μ filters. The filtered supernatant was concentrated by centrifuging at 100,000 rpm for 10 minutes. After centrifugation, the supernatant was discarded and the pellet was suspended in suspension buffer and assayed for reverse transcriptase activity.

Reverse transcriptase activity was detected using a PCR based described in Maudru and Peden 1997, Journal of Virological Methods, 66: 247–261.

Materials and Methods:

A reverse transcriptase step (Reverse Transcription System from Promega, Madison, Wis.) was performed using 11.4 μL of concentrated stromal culture supernatant prepared as described above. Tubes with a total reaction volume of 25 μL contained the supernatant and the following reaction components: 10 mM Tris-HCl, pH 8.3, 50 mM KCl, 5 mM MgCl2, 0.2 mM dNTP, 2 μM DTT and 0.35% Triton X-100, 8U Rnasin, 9 pmol of M1 primer (Integrated DNA Technologies, Inc.), and 300 ng RNA template (MS2 RNA from Boehringer Mannheim, Indianapolis, Ind.). The tubes were incubated at 37° C. for 5 hours. Along with these samples, the appropriate assay controls e.g., positive control and –RNA control, were used.

Polymerase Chain Reaction (PCR) was performed using 50 μL as a total reaction volume. The 5 μL cDNA was mixed with 20 μL nuclease free water. The residual RNA was digested by incubating at 37° C. in the presence of 8 ng of RNAse. After RNA digestion, the master mix containing the 10 mM Tris-HCl, PH 8.3, 50 mM KCl, 2.5 mM MgCl2, 200 μM each dNTP, 1 mM DTT, 0.175% Triton X-100, 25 pmoles of M2 primer (Integrated DNA Technologies, Inc.), 14 pmoles of M1 primer (Integrated DNA Technologies, Inc.), 2.5 units of Ampli Taq DNA polymerase (Perkin Elmer Biosystems, Foster City, Calif.). The tubes were placed in a thermo cycler and the products were amplified by using the following PCR conditions. The products were amplified by 1 cycle at 94° C. for 1 minute and 35 cycles at 94° C. for 30 s, 56° C. for 30 s, 72° C. for 30 s. The final extension was done at 72° C. for 10 minutes.

The amplified products were evaluated using Agarose Gel Electrophoresis. A 2% agarose gel was prepared and the PCR products were loaded and the electrophoresis was carried out in the presence of ethidium bromide at 90 v for 45 minutes. The gels were photographed under UV light using a Polaroid camera. The results are represented in FIG. 6 Section 4, supra.

The amplified products were also evaluated using an ELISA based detection system. The biotin labeled capture probe was coated on to Avidin coated microtitre plates. The PCR products were first hybridized to the capture probe and then to the digoxin labeled detector probe. Bound digoxin was detected with peoxidase labeled anti-digoxin Fab fragments. The enzymatic reaction was carried out with ABTS solution as a substrate. The absorbance was measured at 405 nM using 490 nM as a reference.

Figure 8:
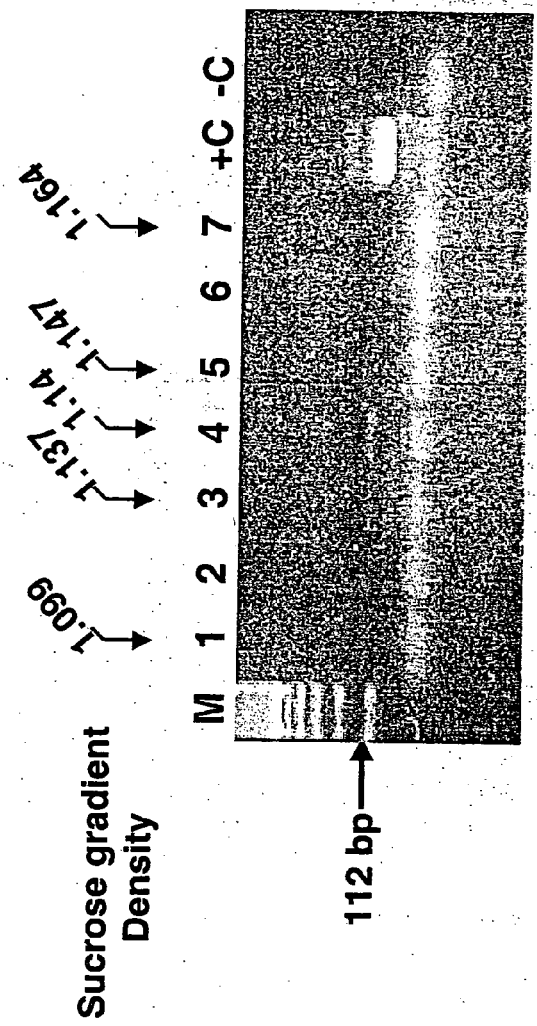
FIG. 8 shows the result of sucrose gradient fractionation of BM culture supernatant taken from MDS patients. The reverse transcriptase activity is highest in a fraction with 1.14 as its density.

Identification of Isopicnic Density of Retrovirus in Bone Marrow Culture Supernatants The filtered stromal culture supernatant which was found positive for reverse transcriptase activity was layered on top of a linear sucrose density gradient solution. The sample was centrifuged at 24000 rpm for 20–24 hours. After the centrifugation, 1 ml fractions were made. The reverse transcriptase activity was measured in these fractions after concentrating 10 times using the ultra centrifugation method described above. It was found that the highest activity was in a fraction with 1.14 as its density. See FIG. 8 Section 4, supra.

Identification of Novel Retroviral POL Sequences

Bone marrow biopsies from MDS patients are grown in culture as described supra, and the supernatant with reverse transcriptase activity is collected and centrifuged.

Once a "viral pellet" had been derived by ultra-centrifugation, total RNA was extracted and converted to cDNA using random primers and reverse transcriptase (RT). Primers are designed for RT-PCR of the viral genome. From well-conserved oligonucleotide sequences from known retroviral sequences were identified and synthetic primers were designed based on these conserved sequences. Synthetic oligonucleotide sequences 5'-RWRMAWRTCRTCCATR-TAHTG-3'(SEQ ID NO:13); 5'-RSAADGTDYTDCCN-CARGG-3'(SEQ ID NO:14'); 5'-CCTYGNGGHAR-HACHTTSYA-3'(SEQ ID NO:15); and 5'-GTNTTYSYMRTNAARAARRMR-3'(SEQ ID NO: 16) were generated and used for primers and probes. Modified consensus primers initially reported by Rush et al. to amplify the RT gene of all known retroviruses is also used to amplify a portion of the putative novel retrovirus. Novel nucleotide sequences are amplified from the hematopoietic cells of MDS patients.

PCR primers from the novel sequence are constructed using MacVector™ 6.0. These primers are subsequently used to perform RT-PCR and PCR studies on nucleic acid extracted from samples of patients with MDS.

RNA extraction and cDNA synthesis of virus preparation from bone marrow culture samples using PCR amplification of cDNA is carried out using degenerate oligonucleotide primers complementary to conserved regions of a retroviral reverse transcriptase gene. The PCR products are cloned and sequenced as described herein. Blast search analysis of nucleotide sequences and selection of novel clones repeatedly observed in MDS hematopoietic cells is carried out. Oligonucleotide primers complementary to the sequence of the novel MDS pol clone are synthesized and used in PCR and RT-PCR studies of samples derived from patients with MDS or acute leukemias. PCR amplification of MDS cDNA using degenerate retroviral pol oligonucleotide primers is also conducted. Novel clones with near identity to MDS pol clone are identified. cDNA library from MDS patients with demonstrable RT-PCR evidence of novel clone in their samples are constructed and screened by Genetrapper™ (Gibco BRL) using oligonucleotide primers complementary to novel clone.

Materials and Methods

1. Isolation of cDNA from virus preparation from bone marrow samples

Protocol 1: Virus Preparation and RNA Extraction

The samples are centrifuged at 2,500 rpm (600 gm) for 20 min at 4° C. to remove the cell debris. The supernatant is transferred to a clean ultracentrifuge tube and the tubes are balanced with a solution contained 50 mM Tris-HCl, pH 8.0/100 mM NaCl/1 mM EDTA. After centrifuging at 9,000 rpm with SW28 Rotor for 25 min at 4° C., the supernatant is transferred to a second ultracentrifuge and centrifuged at 28,000 rpm for 4.5 hours with the same rotor. The pellet is suspended with 150 ul DNAse solution (RNAse free DNAse 5 ul/RNasin 0.2 ul/10 mg/ml yeast tRNA 1 ul) and digested at RT for 20 min. 50 ul of "proteinase K solution" containing 1 ul of 10 mg/ml of Proteinase K and 0.5 ul of 20% SDS is added and the mixture is incubated at 55° C. for 20 minutes.

After incubation, 600 ul Trizol LS solution is added to each tube and mixed well. After letting the tubes sit for 10 min at room temperature, 160 ul of Chloroform is added and the tubes are vigorously shaken by hand for 15 seconds. After incubation at room temperature for 5 minutes, the tubes are centrifuged at 12,000 gm for 15 minutes at 4° C. The colorless upper aqueous phase is transferred to a clean tube and the RNA is precipitated overnight with 0.4 ml of isopropyl alcohol at –70° C. The tubes are centrifuged at 12,000 gm at 4° C. in the next morning after warming up to room temperature for 5–10 minutes. To wash the RNA, 75% ethanol in the DEPC water is layered onto the pellet and the tube is centrifuged at 7,500 gm twice.

The pellet is air dried and dissolved in 20 ul of RNAse free water. Immediately after this step, the RNA is reverse transcribed to cDNA.

cDNA Synthesis of RNA Extracted from Virus Preparation

The RNA extracted from the samples was reverse transcribed to cDNA.

Protocol 2: cDNA synthesis 3.8 ul of 6mers random primer solution (0.5 ul of 20 uM primer/0.3 ul of RNAsin/3 ul of RNAse free water) are mixed with 9 ul of RNA extracts from bone marrow. The RNA is denatured at 75° C. for 10 minutes with the random primers and chilled on ice for 2–3 minutes. 7.2 ul of M-MLV reaction mix (4 ul of 5×1 st strain buffer/2 ul of 100 mM DTT/0.8 ul M-MLV reverse transcriptase/0.4 ul of 25 mM dNTPs) is added to the tube, mixed well, centrifuged briefly, and incubated at 37° C. for 1 hour. The enzyme is inactivated for 5 minutes at 95° C. and the cDNA is stored at –20° C.

2. PCR Amplification of Conserved Retroviral Pol Gene

The cDNA samples (protocol 2) are used as substrate for the PCR amplification of the retroviral pol gene. This highly conserved region of the reverse transcriptase gene is amplified using a modification of the oligonucleotide primers. Using this protocol, the majority of known exogenous and endogenous retroviral pol genes can be amplified.

Protocol 3: PCR Amplification

PCR Recipe
5 ul of 10×PCR buffer without magnesium
5 ul of 25 mM MgCl/0.4 ul of 25 mM dNTPs
1 ul of 20 uM of each primer
0.5 ul (1 unit) of Taq polymerase
1 ul of cDNA and 35.1 ul of water
50 ultotal reaction volume The DNA amplified fragment is identified after electrophoresis on a 3% agarose gel by ethidium bromide staining from cDNA samples and the MDS cDNA sample. Each product is purified from the gel by gel extraction and cloned.

3. PCR Studies of Samples Using MDS Primers

The RNA is extracted from patients with MDS or acute leukemias and reverse transcribed to cDNA as described previously (protocol 2) with M-MLV reverse transcriptase using 6 mers as random primers. The PCR products are separated on a 3% of agarose gel and transferred to a nylon membrane. The membrane is hybridized with MDS internal oligo probe (protocol 4).

Protocol 4: Southern Blot and Hybridization

The PCR products are separated on an agarose gel and transferred to a nylon membrane overnight in an alkali buffer containing 1.5 M NaCl and 0.5 M NaOH. The membranes are neutralized in neutralizing buffer and the PCR products are crosslinked to the membrane.

The MDS internal oligoprobe is labeled with P[32] by polynucleotide kinase and hybridized to the membrane at 42° C. overnight in 20% formamide. The membranes are washed using 2×SSC/0.1% SDS for 10 min at RT, 1×SSC/0.1% SDS, 10 min twice, then 0.5×SSC/0.1% SDS 10 min twice at room temperature. The membrane is exposed to Hyperfilm overnight at –70° C.

Recognition of Viral Antigens by Antibodies

In order to determine whether viral antigens are recognized by antibodies present in a patient's sera, several immunoprecipitation experiments are carried out. Cells infected with virus are labeled with .sup.35 S methionine. Cells are lysed and a cytoplasmic extract is made. Labeled virus released in the supernatant is banded in a sucrose gradient. Materials are immunoprecipitated by serum samples. The resulting immunocomplexes are analyzed by polyacrylamide gel electrophoresis under denaturing conditions.

The MDS associated virus can be recognized by sera of patients with MDS Any immunological assay can be utilized. Immunofluorescence or immunoenzymatic assays or radio-immunoprecipitation tests are examples.

Labeled viral extracts are deposited into wells of a titration microplate, serum from patients is introduced in varying dilutions into the wells. The microplate is incubated and washed extensively. Then, labeled antibodies are introduced into the wells and the amount of substrate hydrolysis is compared to that of a control well.

By example, an ELISA test is used for the detection and titration of seric anti-MDS associated retrovirus antibodies. It comprises carrying out a competition test between the viral antigen and a control antigen constituted by a lysate of the same though non-infected cells.

The binding of the antibodies on the two antigens is revealed by the use of a human antiglobulin labeled with an enzyme which itself is revealed by the addition of a corresponding substrate.

Preparation of the Viral Antigen

The cellular cultures are prepared from bone marrow as described above. After infection of cells by virus, the supernatant of the infected cell culture is concentrated by precipitating with 10% PEG, then purified two or three times on a 20–60% sucrose gradient by ultracentrifugation to equilibrium.

The viral fractions are gathered and concentrated by centrifugation at 50,000 rotations per minute for 60 minutes. The sedimented virus is taken in a minimum volume of buffer NTE at pH7.4 (Tris 0.01M, NaCl 0.1 M, EDTA 0.0001M). The protein concentration is determined by the Lowry method. The virus is lysed by a RIPA and SDS buffer.

Preparation of the Control Antigen

Non-infected cells are cultured according to the preceding conditions and are centrifuged and lysed. The lysate is centrifuged and the supernatant which constitutes the control antigen is collected. The protein concentration is measured by the Lowry method.

Preparation of the Plates

Several dilutions of viral and control antigen are distributed into NUNC plates. The plates are incubate overnight at 4° C. Then distilled water is added and the plates are centrifuged. The wells of the plate are then filled with non-fetal calf serum in PBS buffer and incubated 2 hours at 37° C. The plates are washed 3 times in PBS buffer with TWEEN20, 0.05% (PBS-tw buffer). The plates are dried and sealed with an adhesive plastic film and stored at –80° C.

ELISA Reaction: Antibody Titer Assay

After defreezing, the plates are washed 3 times in PBS-TWEEN and carefully dried. The positive and negative sera are diluted and deposited in duplicate on viral antigen and on control antigen. The plates are incubated and washed and carefully dried.

Revealing the enzymatic reaction is a orthophenylenediamine substrate, which is deposited into each well. The plates are left in a dark room for 20 minutes and a reading is carried out on a spectrophotometer at 492 nm. Sera deemed as containing antibodies against the virus are those which give a ODD (optical density difference–optical density of viral antigen less optical density of control antigen) equal to or higher than 0.30.

Localization of the Retrovirus By In-Situ Hybridization

The following method was used to study sub cellular localization of virally encoded message by pre-embedding in situ hybridization using colloidal gold as an electron dense marker. This methodology was very useful for correlating cellular and viral nucleic acid localization with the viral particles at the electron microscope level.

6.5.1 Materials and Methods

Cells were fixed in 5% Buffered Formalin for 24 h. Cells were washed with 0.04% DEPC/PBS by suspending and centrifugation (in 5 cc tubes) eppendorff. Then the cells were incubated for 10 min at room temperature in 0.02% TritonX-100. The wash step with 0.04% DEPC/PBS was repeated and cells were incubated in Proteinase K solution (0.5 mg 1 mL) at room temperature for 10 min. The wash step was repeated and the cells were prepared for hybridization.

Following hybridization, cells were washed (in 1.5 ml Eppendorf tube) as follows: two washes for 30 seconds in 0.02% Triton X; one wash for 10 minutes in 0.2×SSC; two washes for 30 seconds in 0.02% Triton X; and one wash for 30 seconds in PBS/1% BSA.

1–2 drops of cell suspension were placed on a silane coated slide, and gently treated with ABC/DAB and $H_2O_2$. The remaining cell suspension was treated with Immuno-Au. Immuno-Au was diluted from 26 ug/ml to 10 uglmL with 1% BSA/PBS and the cell suspension was incubated in 1 part diluted Immuno-AU: 2 parts 1% BSA/PBS at room temperature overnight. Cells were washed 2×in DEPCPBS and post-fixed with 3% agar, cut into small pieces and treated for routine EM visualization.

6.5.2 In Situ Examination of Bone Marrow Biopsies by Electron Microscopy

Materials:

0.2 Cacodylate Buffer Stock:

21.4020 g Cacodylate was added to 450 ml water and dissolved with a magnetic stirrer and the total volume is brought up to 500 m with water. The pH was adjusted using HCl to 7.4.

Glutaraldehyde Fixative
50 ml 0.2M Sodium Cacodylate Buffer
10 ml 25% Glutaraldehyde
40 ml Distilled H2O 5% Uranyl Acetate Stock
2.5 g Uranyl Acetate
50 mlH2O The solution was warmed on a stirrer/heater on the minimum setting to help dissolved UA and then cooled and filtered.

Embedding Formula

Araldite 506 (48 g), Embed 812 (52 g), and DDSA (10 g) were mixed well. Then 4 ml of DMP-30 (Accelerator) was added and mixed for an additional 15 minutes.

Osmium Tetroxide 1 g of Osmium (crystals) was added to 100 ml of 0.1 M Cacodylate Buffer, stirred well and frozen. Before use, the osmium preparation was stirred for one hour.

Results

Bone marrow biopsies were subjected to a dissecting procedure whereby the bony pieces were dissected out from a large core biopsy and the separated marrow, which consists of both the parenchymal cells and the stroma, was fixed in 3% Glutaraldehyde.

The marrow was fixed in 3% Glutaraldehyde for a period of three hours at 4° C. and then washed three times with 0.1 M Cacodylate buffer. The marrow was then post-fixed in osmium tetroxide for one hour at 4° C. The marrow was fixed again in 3% Glutaraldehyde and washed three times with 0.1 M cacodylate buffer after which 70% ethynol was added to the marrow and routine electron microscopy was carried out using a standard procedure which is described as follows:

Tissue Processing for Electron Microscopy

Sodium Cacodylate Fixative, 0.2M 2–3 hours room temp, or overnight in the refrigerator
Cacodylate Wash 3×, 10 minutes, each wash
Osmium Tetroxide Fixative 19 minutes, room temperature
Distilled Water Wash 3–4×, 5–10 minutes, each wash
Uranyl Acetate 1%, EM Block Stain 90 minutes, covered from light
70% Ethanol 10 minutes, 2×
95% Ethanol " "
100% Ethanol " "
Propylene Oxide " "
50/50 of Propylene Oxide/Epoxy 2 hours, covered
Remove covers/lids and leave rotating overnight.
100% Fresh Epoxy 3 hours is soft vacuum* in molds.
60 Degree Oven 48 hours * Soft vacuum: put tissue in embedding molds into desiccator, plug pump into wall for approximately 30 seconds. Turn top to seal before unplugging pump.

Equivalents

It will be appreciated that the methods and compositions of the present invention are capable of being incorporated in the form of a variety of embodiments, only a few of which have been illustrated and described above. While specific examples have been provided, the above description is illustrative and not restrictive. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within the scope of the invention.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into a least equal halves, thirds, quarters , fifths, tenths etc. As a non-limiting example, each range discussed herein can be readily broken down in to a lower middle third, middle third and upper third, As will also be understood by one skilled in the art all language such as "up to," "at least," "greater than," "more than" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Accordingly, for all purposes,the present invention encompasses not only the main group, but also the main group absent one or more of the group members, The present invention also envisages the explicit exclusion of one or more of any of the group members in the claimed invention.

All publications and patent document cited in this application are incorporated by reference in their entirety for all purposes to the same extent as if each individual publication or patent document were so individually denoted.

What is claimed is:

1. A method for identifying the presence of a myelodysplastic syndrome associated retrovirus in a biological sample comprising detecting the presence or absence of the myelodysplastic syndrome associated retrovirus in the biological sample.

2. The method of claim 1 wherein the step of detecting the presence or absence of the myelodysplastic syndrome associated retrovirus in the biological sample comprises detecting the presence or absence of myelodysplastic syndrome associated retroviral nucleic acid specific to the myelodysplastic syndrome associated retrovirus in the biological sample, wherein the presence of the myelodysplastic syndrome associated retroviral nucleic acid specific to the myelodysplastic syndrome associated retrovirus indicates that the biological sample is infected with the myelodysplastic syndrome associated retrovirus.

3. The method of claim 1 wherein the step of detecting the presence or absence of the myelodysplastic syndrome associated retrovirus in the biological sample comprises visually identifying the presence or absence of the myelodysplastic syndrome associated retrovirus in the biological sample, wherein the presence of viral particles indicates that the biological sample is infected with the myelodysplastic syndrome associated retrovirus.

4. The method of claim 1 wherein the step of detecting the presence or absence of the myelodysplastic syndrome associated retrovirus in the biological sample comprises contacting the biological sample with a fragment of an antibody which is capable of detecting the presence of the myelodysplastic syndrome associated retrovirus and determining whether the antibody detected the presence of the myelodysplastic syndrome associated retrovirus.

5. The method of claim 1 further comprising obtaining the biological sample from an individual.

6. The method of claim 4 wherein the antibody capable of detecting the presence of the myelodysplastic syndrome associated retrovirus is capable of detecting a gene product of the myelodysplastic syndrome associated retrovirus.

7. The method of claim 5 wherein the individual is suspected of having myelodysplastic syndrome or chronic leukemia.

8. A human myelodysplastic syndrome associated virus isolated from ATCC Deposit No. PTA-2733 or PTA-2734.

9. An isolated myelodysplastic syndrome associated retrovirus comprised of a viral particle size ranging from 40 to 60 nm and a density of 1.14 to 1.16 as measured by a sugar density gradient with the proviso that the virus is not HIV, HTLV or MMTV.

10. A method for isolating myelodysplastic syndrome associated retrovirus comprising:

(a) culturing cells infected with myelodysplastic syndrome associated retrovirus;

(b) collecting supernatant of said cultured cells;

(c) separating the components in the supernatant on a sucrose density gradient; and (d) isolating the separated components that have retroviral activity.

11. The method of claim 10 wherein the cultured cells are infected with the myelodysplastic syndrome retrovirus, wherein the myelodysplastic syndrome retrovirus comprises either human myelodysplastic syndrome associated retrovirus isolated from ATCC Deposit No. PTA-2733 or PTA-2734 or an isolated myelodysplastic syndrome associated retrovirus comprised of a viral particle size ranging from 40 to 60 nm and a density of 1.14 to 1.16 as measured by a sugar density gradient with the proviso that the virus is not HIV, HTLV or MMTV.

12. The method of claim 10 wherein the cultured cells are stromal fibroblasts.

13. A myelodysplastic syndrome associated retrovirus isolated according to the method of claim 10.

14. An isolated antibody that binds to the virus of claim 8, 9 or 12 or a gene product thereof.

15. A kit for detecting a myelodysplastic syndrome associated retrovirus comprising instructions for carrying out the method of any one of claims 1, 2–6, 10 or 12.

16. The kit of claim 15 further comprising one or more reagents for performing the method set forth in the instructions.

* * * * *